United States Patent
Liu et al.

(10) Patent No.: US 11,597,958 B2
(45) Date of Patent: Mar. 7, 2023

(54) DNA ASSEMBLY METHOD AND ITS APPLICATION

(71) Applicant: Nanjing Zhongkeyouzi Institute of Biotechnology Co., Ltd., Jiangsu (CN)

(72) Inventors: Shuwen Liu, Jiangsu (CN); Tingyi Wen, Jiangsu (CN); Yun Zhang, Jiangsu (CN); Aihua Deng, Jiangsu (CN)

(73) Assignee: NANJING ZHONGKEYOUZI INSTITUTE OF BIOTECHNOLOGY CO., LTD, Jiangsu (CN)

( * ) Notice: Subject to any disclaimer, the term of this patent is extended or adjusted under 35 U.S.C. 154(b) by 23 days.

(21) Appl. No.: 16/724,679

(22) Filed: Dec. 23, 2019

(65) Prior Publication Data

US 2020/0208188 A1    Jul. 2, 2020

(30) Foreign Application Priority Data

Dec. 27, 2018  (CN) .......................... 201811613376.4

(51) Int. Cl.
*C12P 19/34*  (2006.01)
*C12N 15/11*  (2006.01)

(52) U.S. Cl.
CPC .............. *C12P 19/34* (2013.01); *C12N 15/11* (2013.01)

(58) Field of Classification Search
CPC ........ C12N 15/11; C12N 15/63; C12N 15/66; C12Q 2521/313; C12Q 2521/501; C12P 19/34
USPC .... 435/6.1, 91.1, 91.31, 455, 458; 536/23.1, 536/24.5
See application file for complete search history.

(56) References Cited

U.S. PATENT DOCUMENTS

2019/0323017 A1* 10/2019 Grimon .................. C12N 15/66

FOREIGN PATENT DOCUMENTS

WO    WO-2008095927 A1 *  8/2008  ............. C12N 15/10

OTHER PUBLICATIONS

Shetty et al., "Engineering BioBrick vectors from BioBrick parts", Journal of Biological Engineering, 2:5, 12 pages, 2008.
Anderson et al. "BglBricks: A flexible standard for biological part assembly", Journal of Biological Engineering, 4:1, 12 pages, 2010.
Lui et al., "iBrick: A New Standard for Iterative Assembly of Biological Parts with Homing Endonucleases", PLOS One, vol. 9, Issue 10, 10 pages Oct. 2014.
Li et al., "C-Brick: A New Standard for Assembly of Biological Parts using Cpf1", ACS Synthetic Biology, 15 pages, Jun. 2016.
Wong et al., "YaliBricks, a versatile genetic toolkit for streamlined and rapid pathway engineering in Yarrowia lipolytica", Metabolic Engineering Communications 5, pp. 68-77, 2017.
Ho et al., "Site-directed mutagenesis by overlap extension using the polymerase chain reaction", Gene, 77, pp. 51-59, 1989.
Martinez-Garcia et al., "SEVA 2.0: an update of the Standard European Vector Architecture for de-/re-construction of bacterial functionalities", Nucleic Acids Research, vol. 43, pp. D1183-D1189, 2015.
Jiang et al., "Multigene Editing in the Escherichia coli Genome via the CRISPR-Cas9 System" AEM, vol. 81, No. 7, pp. 2506-2514, Apr. 2015.

* cited by examiner

*Primary Examiner* — Jane J Zara
(74) *Attorney, Agent, or Firm* — Panitch Schwarze Belisario & Nadel LLP; Stephany G. Small; Travis W. Bliss

(57) ABSTRACT

The invention relates to a plasmid, a DNA assembly method and its application recombinant strain. The plasmid has single adjacent Type IIP and Type IIS RE recognition sites. The plasmid combines the properties of Type IIP and Type IIS REs to achieve recursive cycling, SCAR-free and repeat sequence assembly.

7 Claims, 6 Drawing Sheets

Specification includes a Sequence Listing.

SEQUENCE LISTING

<160> NUMBER OF SEQ ID NOS: 134

<210> SEQ ID NO 1
<211> LENGTH: 2686
<212> TYPE: DNA
<213> ORGANISM: Artificial Sequence
<220> FEATURE:
<223> OTHER INFORMATION: plasmid pUC19

<400> SEQUENCE: 1

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt cgagctcggt acccggggat    420
cctctagagt cgacctgcag gcatgcaagc ttggcgtaat catggtcata gctgtttcct    480
gtgtgaaatt gttatccgct cacaattcca cacaacatac gagccggaag cataaagtgt    540
aaagcctggg gtgcctaatg agtgagctaa ctcacattaa ttgcgttgcg ctcactgccc    600
gctttccagt cgggaaacct gtcgtgccag ctgcattaat gaatcggcca acgcgcgggg    660
agaggcggtt tgcgtattgg gcgctcttcc gcttcctcgc tcactgactc gctgcgctcg    720
gtcgttcggc tgcggcgagc ggtatcagct cactcaaagg cggtaatacg gttatccaca    780
gaatcagggg ataacgcagg aaagaacatg tgagcaaaag gccagcaaaa ggccaggaac    840
cgtaaaaagg ccgcgttgct ggcgtttttc cataggctcc gcccccctga cgagcatcac    900
aaaaatcgac gctcaagtca gaggtggcga acccgacag gactataaag ataccaggcg    960
tttccccctg gaagctccct cgtgcgctct cctgttccga ccctgccgct taccggatac   1020
ctgtccgcct ttctcccttc gggaagcgtg gcgctttctc atagctcacg ctgtaggtat   1080
ctcagttcgg tgtaggtcgt tcgctccaag ctgggctgtg tgcacgaacc ccccgttcag   1140
cccgaccgct gcgccttatc cggtaactat cgtcttgagt ccaacccggt aagacacgac   1200
ttatcgccac tggcagcagc cactggtaac aggattagca gagcgaggta tgtaggcggt   1260
gctacagagt tcttgaagtg gtggcctaac tacggctaca ctagaaggac agtatttggt   1320
```

```
atctgcgctc tgctgaagcc agttaccttc ggaaaaagag ttggtagctc ttgatccggc    1380
aaacaaacca ccgctggtag cggtggtttt tttgtttgca agcagcagat tacgcgcaga    1440
aaaaaaggat ctcaagaaga tcctttgatc ttttctacgg ggtctgacgc tcagtggaac    1500
gaaaactcac gttaagggat tttggtcatg agattatcaa aaaggatctt cacctagatc    1560
cttttaaatt aaaaatgaag ttttaaatca atctaaagta tatatgagta aacttggtct    1620
gacagttacc aatgcttaat cagtgaggca cctatctcag cgatctgtct atttcgttca    1680
tccatagttg cctgactccc cgtcgtgtag ataactacga tacgggaggg cttaccatct    1740
ggccccagtg ctgcaatgat accgcgagac ccacgctcac cggctccaga tttatcagca    1800
ataaaccagc cagccggaag ggccgagcgc agaagtggtc ctgcaacttt atccgcctcc    1860
atccagtcta ttaattgttg ccgggaagct agagtaagta gttcgccagt taatagtttg    1920
cgcaacgttg ttgccattgc tacaggcatc gtggtgtcac gctcgtcgtt tggtatggct    1980
tcattcagct ccggttccca acgatcaagg cgagttacat gatcccccat gttgtgcaaa    2040
aaagcggtta gctccttcgg tcctccgatc gttgtcagaa gtaagttggc cgcagtgtta    2100
tcactcatgg ttatggcagc actgcataat tctcttactg tcatgccatc cgtaagatgc    2160
ttttctgtga ctggtgagta ctcaaccaag tcattctgag aatagtgtat gcggcgaccg    2220
agttgctctt gcccggcgtc aatacgggat aataccgcgc cacatagcag aactttaaaa    2280
gtgctcatca ttggaaaacg ttcttcgggg cgaaaactct caaggatctt accgctgttg    2340
agatccagtt cgatgtaacc cactcgtgca cccaactgat cttcagcatc ttttactttc    2400
accagcgttt ctgggtgagc aaaaacagga aggcaaaatg ccgcaaaaaa gggaataagg    2460
gcgacacgga aatgttgaat actcatactc ttccttttt caatattattg aagcatttat    2520 cagggttatt gtctcatgag cggatacata tttgaatgta tttagaaaaa taaacaaata    2580
ggggttccgc gcacatttcc ccgaaaagtg ccacctgacg tctaagaaac cattattatc    2640
atgacattaa cctataaaaa taggcgtatc acgaggccct ttcgtc                    2686

<210> SEQ ID NO 2
<211> LENGTH: 711
<212> TYPE: DNA
<213> ORGANISM: Artificial Sequence
<220> FEATURE:
<223> OTHER INFORMATION: mCherry gene

<400> SEQUENCE: 2
atggtgagca agggcgagga ggataacatg gccatcatca aggagttcat gcgcttcaag     60
gtgcacatgg agggctccgt gaacggccac gagttcgaga tcgagggcga gggcgagggc    120
cgcccctacg agggcaccca gaccgccaag ctgaaggtga ccaagggtgg ccccctgccc    180
ttcgcctggg acatcctgtc ccctcagttc atgtacggct ccaaggccta cgtgaagcac    240
cccgccgaca tccccgacta cttgaagctg tccttcccccg agggcttcaa gtgggagcgc    300
gtgatgaact tcgaggacgg cggcgtggtg accgtgaccc aggactcctc cctgcaggac    360
ggcgagttca tctacaaggt gaagctgcgc ggcaccaact cccctccga cggccccgta    420 atgcagaaga gaccatgggg ctgggaggcc tcctccgagc ggatgtaccc cgaggacggc    480
gccctgaagg gcgagatcaa gcagaggctg aagctgaagg acggcggcca ctacgacgct    540
gaggtcaaga ccacctacaa ggccaagaag cccgtgcagc tgcccggcgc ctacaacgtc    600
aacatcaagt tggacatcac ctcccacaac gaggactaca ccatcgtgga acagtacgaa    660
cgcgccgagg gccgccactc caccggcggc atggacgagc tgtacaagta a              711
```

<210> SEQ ID NO 3
<211> LENGTH: 4245
<212> TYPE: DNA
<213> ORGANISM: Artificial Sequence
<220> FEATURE:
<223> OTHER INFORMATION: plasmid pACYC184

<400> SEQUENCE: 3

```
gaattccgga tgagcattca tcaggcgggc aagaatgtga ataaaggccg gataaaactt     60
gtgcttattt ttctttacgg tctttaaaaa ggccgtaata tccagctgaa cggtctggtt    120
ataggtacat tgagcaactg actgaaatgc ctcaaaatgt tctttacgat gccattggga    180
tatatcaacg gtggtatatc cagtgatttt tttctccatt ttagcttcct tagctcctga    240
aaatctcgat aactcaaaaa atacgcccgg tagtgatctt atttcattat ggtgaaagtt    300
ggaacctctt acgtgccgat caacgtctca ttttcgccaa aagttggccc agggcttccc    360
ggtatcaaca gggacaccag gatttattta ttctgcgaag tgatcttccg tcacaggtat    420
ttattcggcg caaagtgcgt cgggtgatgc tgccaactta ctgatttagt gtatgatggt    480
gtttttgagg tgctccagtg gcttctgttt ctatcagctg tccctcctgt tcagctactg    540
acggggtggt gcgtaacggc aaaagcaccg ccggacatca gcgctagcgg agtgtatact    600
ggcttactat gttggcactg atgagggtgt cagtgaagtg cttcatgtgg caggagaaaa    660
aaggctgcac cggtgcgtca gcagaatatg tgatacagga tatattccgc ttcctcgctc    720
actgactcgc tacgctcggt cgttcgactg cggcgagcgg aaatggctta cgaacggggc    780
ggagatttcc tggaagatgc caggaagata cttaacaggg aagtgagagg gccgcggcaa    840
agccgttttt ccataggctc cgcccccctg acaagcatca cgaaatctga cgctcaaatc    900
agtggtggcg aaacccgaca ggactataaa gataccaggc gtttccccct ggcggctccc    960
tcgtgcgctc tcctgttcct gcctttcggt ttaccggtgt cattccgctg ttatggccgc   1020
gtttgtctca ttccacgcct gacactcagt tccgggtagg cagttcgctc caagctggac   1080
tgtatgcacg aacccccgt tcagtccgac cgctgcgcct tatccggtaa ctatcgtctt   1140
gagtccaacc cggaaagaca tgcaaaagca ccactgcag cagccactgg taattgattt   1200
agaggagtta gtcttgaagt catgcgccgg ttaaggctaa actgaaagga caagttttgg   1260
tgactgcgct cctccaagcc agttacctcg gttcaaagag ttggtagctc agagaacctt   1320
cgaaaaaccg ccctgcaagg cggttttttc gttttcagag caagagatta cgcgcagacc   1380
aaaacgatct caagaagatc atcttattaa tcagataaaa tatttctaga tttcagtgca   1440
atttatctct tcaaatgtag cacctgaagt cagccccata cgatataagt tgtaattctc   1500
atgtttgaca gcttatcatc gataagcttt aatgcggtag tttatcacag ttaaattgct   1560
aacgcagtca ggcaccgtgt atgaaatcta acaatgcgct catcgtcatc ctcggcaccg   1620
tcaccctgga tgctgtaggc ataggcttgg ttatgccggt actgccgggc ctcttgcggg   1680
atatcgtcca ttccgacagc atcgccagtc actatggcgt gctgctagcg ctatatgcgt   1740
tgatgcaatt tctatgcgca cccgttctcg gagcactgtc cgaccgcttt ggccgccgcc   1800
cagtcctgct cgcttcgcta cttggagcca ctatcgacta cgcgatcatg gcgaccacac   1860
ccgtcctgtg gatcctctac gccggacgca tcgtggccgg catcaccggc gccacaggtg   1920
cggttgctgg cgcctatatc gccgacatca ccgatgggga gatcgggct cgccacttcg   1980
ggctcatgag cgcttgtttc ggcgtgggta tggtggcagg ccccgtggcc ggggggactgt   2040
```

```
tgggcgccat ctccttgcat gcaccattcc ttgcggcggc ggtgctcaac ggcctcaacc      2100
tactactggg ctgcttccta atgcaggagt cgcataaggg agagcgtcga ccgatgccct      2160
tgagagcctt caacccagtc agctccttcc ggtgggcgcg gggcatgact atcgtcgccg      2220
cacttatgac tgtcttcttt atcatgcaac tcgtaggaca ggtgccggca gcgctctggg      2280
tcattttcgg cgaggaccgc tttcgctgga gcgcgacgat gatcggcctg tcgcttgcgg      2340
tattcggaat cttgcacgcc ctcgctcaag ccttcgtcac tggtcccgcc accaaacgtt      2400
tcggcgagaa gcaggccatt atcgccggca tggcggccga cgcgctgggc tacgtcttgc      2460
tggcgttcgc gacgcgaggc tggatggcct tccccattat gattcttctc gcttccggcg      2520
gcatcgggat gcccgcgttg caggccatgc tgtccaggca ggtagatgac gaccatcagg      2580
gacagcttca aggatcgctc gcggctctta ccagcctaac ttcgatcatt ggaccgctga      2640
tcgtcacggc gatttatgcc gcctcggcga gcacatggaa cgggttggca tggattgtag      2700
gcgccgccct ataccttgtc tgcctccccg cgttgcgtcg cggtgcatgg agccgggcca      2760
cctcgacctg aatggaagcc ggcggcacct cgctaacgga ttcaccactc caagaattgg      2820
agccaatcaa ttcttgcgga gaactgtgaa tgcgcaaacc aaccctttggc agaacatatc      2880 catcgcgtcc gccatctcca gcagccgcac gcggcgcatc tcgggcagcg ttgggtcctg      2940
gccacgggtg cgcatgatcg tgctcctgtc gttgaggacc cggctaggct ggcggggttg      3000
ccttactggt tagcagaatg aatcaccgat acgcgagcga acgtgaagcg actgctgctg      3060
caaaacgtct gcgacctgag caacaacatg aatggtcttc ggtttccgtg tttcgtaaag      3120
tctgaaaacg cggaagtccc ctacgtgctg ctgaagttgc ccgcaacaga gagtggaacc      3180
aaccggtgat accacgatac tatgactgag agtcaacgcc atgagcggcc tcatttctta      3240
ttctgagtta caacagtccg caccgctgtc cggtagctcc ttccggtggg cgcggggcat      3300
gactatcgtc gccgcactta tgactgtctt ctttatcatg caactcgtag gacaggtgcc      3360
ggcagcgccc aacagtcccc cggcacgggg gcctgccacc atacccacgc cgaaacaagc      3420
gccctgcacc attatgttcc ggatctgcat cgcaggatgc tgctggctac cctgtggaac      3480
acctacatct gtattaacga agcgctaacc gttttttatca ggctctggga ggcagaataa      3540
atgatcatat cgtcaattat tacctccacg gggagagcct gagcaaactg gcctcaggca      3600
tttgagaagc acacggtcac actgcttccg gtagtcaata aaccggtaaa ccagcaatag      3660
acataagcgg ctatttaacg accctgccct gaaccgacga ccgggtcgaa tttgctttcg      3720
aatttctgcc attcatccgc ttattatcac ttattcaggc gtagcaccag gcgtttaagg      3780
gcaccaataa ctgccttaaa aaaattacgc cccgccctgc cactcatcgc agtactgttg      3840
taattcatta agcattctgc cgacatggaa gccatcacag acggcatgat gaacctgaat      3900
cgccagcggc atcagcacct tgtcgccttg cgtataatat ttgcccatgg tgaaaacggg      3960
ggcgaagaag ttgtccatat tggccacgtt taaatcaaaa ctggtgaaac tcacccaggg      4020
attggctgag acgaaaaaca tattctcaat aaaccccttta gggaaatagg ccaggttttc      4080
accgtaacac gccacatctt gcgaatatat gtgtagaaac tgccggaaat cgtcgtggta      4140
ttcactccag agcgatgaaa acgtttcagt ttgctcatgg aaaacggtgt aacaagggtg      4200
aacactatcc catatcacca gctcaccgtc tttcattgcc atacg                      4245

<210> SEQ ID NO 4
<211> LENGTH: 5020
<212> TYPE: DNA
<213> ORGANISM: Escherichia coli
```

<400> SEQUENCE: 4

```
agcttttcat tctgactgca acgggcaata tgtctctgtg tggattaaaa aaagagtgtc      60
tgatagcagc ttctgaactg gttacctgcc gtgagtaaat taaaatttta ttgacttagg     120
tcactaaata ctttaaccaa tataggcata gcgcacagac agataaaaat tacagagtac     180
acaacatcca tgaaacgcat tagcaccacc attaccacca ccatcaccat taccacaggt     240
aacggtgcgg gctgacgcgt acaggaaaca cagaaaaaag cccgcacctg acagtgcggg     300
cttttttttt cgaccaaagg taacgaggta acaaccatgc gagtgttgaa gttcggcggt     360
acatcagtgg caaatgcaga acgttttctg cgtgttgccg atattctgga aagcaatgcc     420
aggcaggggc aggtggccac cgtcctctct gcccccgcca aaatcaccaa ccacctggtg     480
gcgatgattg aaaaaaccat tagcggccag gatgctttac ccaatatcag cgatgccgaa     540
cgtattttg ccgaactttt gacgggactc gccgccgccc agccggggtt cccgctggcg     600
caattgaaaa ctttcgtcga tcaggaattt gcccaaataa acatgtcct gcatggcatt     660
agtttgttgg ggcagtgccc ggatagcatc aacgctgcgc tgatttgccg tggcgagaaa     720
atgtcgatcg ccattatggc cggcgtatta gaagcgcgcg tcacaacgt tactgttatc     780
gatccggtcg aaaaactgct ggcagtgggg cattacctcg aatctaccgt cgatattgct     840
gagtccaccc gccgtattgc ggcaagccgc attccggctg atcacatggt gctgatggca     900
ggtttcaccg ccggtaatga aaaggcgaa ctggtggtgc ttggacgcaa cggttccgac     960
tactctgctg cggtgctggc tgcctgttta cgcgccgatt gttgcgagat ttggacggac    1020
gttgacgggg tctatacctg cgacccgcgt caggtgcccg atgcgaggtt gttgaagtcg    1080
atgtcctacc aggaagcgat ggagctttcc tacttcggcg ctaaagttct tcaccccgc     1140
accattaccc ccatcgccca gttccagatc ccttgcctga ttaaaaatac cggaaatcct    1200
caagcaccag gtacgctcat tggtgccagc cgtgatgaag acgaattacc ggtcaagggc    1260
atttccaatc tgaataacat ggcaatgttc agcgtttctg gtccggggat gaaagggatg    1320
gtcggcatgg cggcgcgcgt ctttgcagcg atgtcacgcg cccgtatttc cgtggtgctg    1380
attacgcaat catcttccga atacagcatc agtttctgcg ttccacaaag cgactgtgtg    1440
cgagctgaac gggcaatgca ggaagagttc tacctggaac tgaaagaagg cttactggag    1500
ccgctggcag tgacgaacg gctggccatt atctcggtgg taggtgatgg tatgcgcacc    1560
ttgcgtggga tctcggcgaa attctttgcc gcactggccc gcgccaatat caacattgtc    1620
gccattgctc agggatcttc tgaacgctca atctctgtcg tggtaaataa cgatgatgcg    1680
accactggcg tgcgcgttac tcatcagatg ctgttcaata ccgatcaggt tatcgaagtg    1740
tttgtgattg gcgtcggtgg cgttggcggt gcgctgctgg agcaactgaa gcgtcagcaa    1800
agctggctga agaataaaca tatcgactta cgtgtctgcg gtgttgccaa ctcgaaggct    1860
ctgctcacca atgtacatgg ccttaatctg gaaaactggc aggaagaact ggcgcaagcc    1920
aaagagccgt ttaatctcgg gcgcttaatt cgcctcgtga agaatatca tctgctgaac    1980
ccggtcattg ttgactgcac ttccagccag gcagtggcgg atcaatatgc cgacttcctg    2040
cgcgaaggtt tccacgttgt cacgccgaac aaaaaggcca cacctcgtc gatggattac    2100
taccatcagt tgcgttatgc ggcggaaaaa tcgcggcgta aattcctcta tgacaccaac    2160
gttgggctg gattaccggt tattgagaac ctgcaaaatc tgctcaatgc aggtgatgaa    2220
ttgatgaagt tctccggcat tctttctggt tcgctttctt atatcttcgg caagttagac    2280
```

```
gaaggcatga gtttctccga ggcgaccacg ctggcgcggg aaatgggtta taccgaaccg    2340
gacccgcgag atgatctttc tggtatggat gtggcgcgta aactattgat tctcgctcgt    2400
gaaacgggac gtgaactgga gctggcggat attgaaattg aacctgtgct gcccgcagag    2460
tttaacgccg agggtgatgt tgccgctttt atggcgaatc tgtcacaact cgacgatctc    2520
tttgccgcgc gcgtggcgaa ggcccgtgat gaaggaaaag ttttgcgcta tgttggcaat    2580
attgatgaag atggcgtctg ccgcgtgaag attgccgaag tggatggtaa tgatccgctg    2640
ttcaaagtga aaatggcga aaacgccctg gccttctata gccactatta tcagccgctg     2700
ccgttggtac tgcgcggata tggtgcgggc aatgacgtta cagctgccgg tgtctttgct    2760
gatctgctac gtaccctctc atggaagtta ggagtctgac atggttaaag tttatgcccc    2820
ggcttccagt gccaatatga gcgtcgggtt tgatgtgctc ggggcggcgg tgacacctgt    2880
tgatggtgca ttgctcggag atgtagtcac ggttgaggcg gcagagacat tcagtctcaa    2940
caacctcgga cgctttgccg ataagctgcc gtcagaacca cgggaaaata tcgtttatca    3000
gtgctgggag cgttttgcc aggaactggg taagcaaatt ccagtggcga tgaccctgga     3060
aaagaatatg ccgatcggtt cgggcttagg ctccagtgcc tgttcggtgg tcgcggcgct    3120 gatgcgatg aatgaacact gcggcaagcc gcttaatgac actcgtttgc tggctttgat     3180
gggcgagctg gaaggccgta ctccggcag cattcattac gacaacgtgg caccgtgttt     3240
tctcggtggt atgcagttga tgatcgaaga aaacgacatc atcagccagc aagtgccagg    3300
gtttgatgag tggctgtggg tgctggcgta tccggggatt aaagtctcga cggcagaagc    3360
cagggctatt ttaccggcgc agtatcgccg ccaggattgc attgcgcacg gcgacatct    3420 ggcaggcttc attcacgcct gctattcccg tcagcctgag cttgccgcga agctgatgaa    3480
agatgttatc gctgaaccct accgtgaacg gttactgcca ggcttccggc aggcgcggca    3540
ggcggtcgcg gaaatcggcg cggtagcgag cggtatctcc ggctccggcc cgaccttgtt    3600
cgctctgtgt gacaagccgg aaaccgccca gcgcgttgcc gactggttgg gtaagaacta    3660
cctgcaaaat caggaaggtt ttgttcatat ttgccggctg gatacggcgg gcgcacgagt    3720
actggaaaac taaatgaaac tctacaatct gaaagatcac aacgagcagg tcagctttgc    3780
gcaagccgta acccaggggt tgggcaaaaa tcaggggctg tttttttccgc acgacctgcc    3840 ggaattcagc ctgactgaaa ttgatgagat gctgaagctg gattttgtca cccgcagtgc    3900
gaagatcctc tcggcgttta ttggtgatga atcccacag gaaatcctgg aagagcgcgt     3960
gcgcgcggcg tttgccttcc cggctccggt cgccaatgtt gaaagcgatg tcggttgtct    4020
ggaattgttc cacgggccaa cgctggcatt taaagatttc ggcggtcgct ttatggcaca    4080
aatgctgacc catattgcgg gtgataagcc agtgaccatt ctgaccgcga cctccggtga    4140
taccggagcg gcagtggctc atgctttcta cggtttaccg aatgtgaaag tggttatcct    4200
ctatccacga ggcaaaatca gtccactgca agaaaaactg ttctgtacat ggggcggcaa    4260
tatcgaaact gttgccatcg acggcgattt cgatgcctgt caggcgctgg tgaagcaggc    4320
gtttgatgat gaagaactga agtggcgct agggttaaac tcggctaact cgattaacat    4380
cagccgtttg ctggcgcaga tttgctacta cttttgaagct gttgcgcagc tgccgcagga    4440
gacgcgcaac cagctggttg tctcggtgcc aagcggaaac ttcggcgatt tgacggcggg    4500
tctgctggcg aagtcactcg gtctgccggt gaaacgtttt attgctgcga ccaacgtgaa    4560
cgataccgtg ccacgtttcc tgcacgacgg tcagtggtca cccaaagcga ctcaggcgac    4620
gttatccaac gcgatggacg tgagtcagcc gaacaactgg ccgcgtgtgg aagagttgtt    4680
```

| | | |
|---|---|---|
| ccgccgcaaa atctggcaac tgaaagagct gggttatgca gccgtggatg atgaaaccac | 4740 | |
| gcaacagaca atgcgtgagt taaaagaact gggctacact tcggagccgc acgctgccgt | 4800 | |
| agcttatcgt gcgctgcgtg atcagttgaa tccaggcgaa tatggcttgt tcctcggcac | 4860 | |
| cgcgcatccg gcgaaattta aagagagcgt ggaagcgatt ctcggtgaaa cgttggatct | 4920 | |
| gccaaaagag ctggcagaac gtgctgattt acccttgctt tcacataatc tgcccgccga | 4980 | |
| ttttgctgcg ttgcgtaaat tgatgatgaa tcatcagtaa | 5020 | |

<210> SEQ ID NO 5
<211> LENGTH: 1570
<212> TYPE: DNA
<213> ORGANISM: Escherichia coli

<400> SEQUENCE: 5

| | | |
|---|---|---|
| ccagatcgat tctgacaaca aactgggcgt aggttcagac gacaccgttg ctgtgggtat | 60 | |
| cgtttaccag ttctaatagc acacctcttt gttaaatgcc gaaaaaacag gactttggtc | 120 | |
| ctgttttttt tataccttcc agagcaatct cacgtcttgc aaaaacagcc tgcgttttca | 180 | |
| tcagtaatag ttggaatttt gtaaatctcc cgttaccctg atagcggact tcccttctgt | 240 | |
| aaccataatg gaacctcgtc atgtttgaga acattaccgc cgctcctgcc gacccgattc | 300 | |
| tgggcctggc cgatctgttt cgtgccgatg aacgtcccgg caaaattaac ctcgggattg | 360 | |
| gtgtctataa agatgagacg ggcaaaaccc cggtactgac cagcgtgaaa aaggctgaac | 420 | |
| agtatctgct cgaaaatgaa accaccaaaa attacctcgg cattgacggc atccctgaat | 480 | |
| ttggtcgctg cactcaggaa ctgctgtttg gtaaaggtag cgccctgatc aatgacaaac | 540 | |
| gtgctcgcac ggcacagact ccgggggggca ctggcgcact acgcgtggct gccgatttcc | 600 | |
| tggcaaaaaa taccagcgtt aagcgtgtgt gggtgagcaa cccaagctgg ccgaaccata | 660 | |
| agagcgtctt taactctgca ggtctggaag ttcgtgaata cgcttattat gatgcggaaa | 720 | |
| atcacactct tgacttcgat gcactgatta acagcctgaa tgaagctcag gctggcgacg | 780 | |
| tagtgctgtt ccatggctgc tgccataacc caaccggtat cgaccctacg ctggaacaat | 840 | |
| ggcaaacact ggcacaactc tccgttgaga aaggctggtt accgctgttt gacttcgctt | 900 | |
| accagggttt tgcccgtggt ctggaagaag atgctgaagg actgcgcgct ttcgcggcta | 960 | |
| tgcataaaga gctgattgtt gccagttcct actctaaaaa ctttggcctg tacaacgagc | 1020 | |
| gtgttggcgc ttgtactctg gttgctgccg acagtgaaac cgttgatcgc gcattcagcc | 1080 | |
| aaatgaaagc ggcgattcgc gctaactact ctaacccacc agcacacggc gcttctgttg | 1140 | |
| ttgccaccat cctgagcaac gatgcgttac gtgcgatttg gaacaagag ctgactgata | 1200 | |
| tgcgccagcg tattcagcgt atgcgtcagt tgttcgtcaa tacgctgcag gaaaaaggcg | 1260 | |
| caaaccgcga cttcagctttt atcatcaaac agaacggcat gttctccttc agtggcctga | 1320 | |
| caaaagaaca agtgctgcgt ctgcgcgaag agtttgcgt atatgcggtt gcttctggtc | 1380 | |
| gcgtaaatgt ggccgggatg acaccagata acatggctcc gctgtgcgaa gcgattgtgg | 1440 | |
| cagtgctgta agcattaaaa acaatgaagc ccgctgaaaa gcgggctgag actgatgaca | 1500 | |
| aacgcaaacat tgcctgatgc gctacgctta tcaggcctac gcgtcccctg caatattttg | 1560 | |
| aatttgcacg | 1570 | |

<210> SEQ ID NO 6
<211> LENGTH: 1622
<212> TYPE: DNA

<213> ORGANISM: Escherichia coli

<400> SEQUENCE: 6

```
cagcatatga tctcgggtat tcggtcgatg caggggataa tcgtcggtcg aaaaacattc      60
gaaaccacat atattctgtg tgtttaaagc aaatcattgg cagcttgaaa agaaggttc     120
acatgtcaaa caacattcgt atcgaagaag atctgttggg taccagggaa gttccagctg    180
atgcctacta tggtgttcac actctgagag cgattgaaaa cttctatatc agcaacaaca    240
aaatcagtga tattcctgaa tttgttcgcg gtatggtaat ggttaaaaaa gccgcagcta    300
tggcaaacaa agagctgcaa accattccta aaagtgtagc gaatgccatc attgccgcat    360
gtgatgaagt cctgaacaac ggaaaatgca tggatcagtt cccggtagac gtctaccagg    420
gcggcgcagg tacttccgta acatgaaca ccaacgaagt gctggccaat atcggtctgg     480
aactgatggg tcaccaaaaa ggtgaatatc agtacctgaa cccgaacgac catgttaaca    540
aatgtcagtc cactaacgac gcctacccga ccggtttccg tatcgcagtt tactcttccc    600
tgattaagct ggtagatgcg attaaccaac tgcgtgaagg ctttgaacgt aaagctgtcg    660
aattccagga catcctgaaa tgggtcgta cccagctgca ggacgcagta ccgatgaccc     720
tcggtcagga attccgcgct ttcagcatcc tgctgaaaga agaagtgaaa aacatccaac    780
gtaccgctga actgctgctg aagttaacc ttggtgcaac agcaatcggt actggtctga     840
acacgccgaa agagtactct ccgctggcag tgaaaaaact ggctgaagtt actggcttcc    900
catgcgtacc ggctgaagac ctgatcgaag cgacctctga ctgcggcgct tatgttatgg    960
ttcacggcgc gctgaaacgc ctggctgtga agatgtccaa aatctgtaac gacctgcgct   1020
tgctctcttc aggcccacgt gccggcctga acagatcaa cctgccggaa ctgcaggcgg    1080
gctcttccat catgccagct aaagtaaacc cggttgttcc ggaagtggtt aaccaggtat   1140
gcttcaaagt catcggtaac gacaccactg ttaccatggc agcagaagca ggtcagctgc   1200
agttgaacgt tatggagccg gtcattggcc aggccatgtt cgaatccgtt cacattctga   1260
ccaacgcttg ctacaaccctg ctggaaaaat gcattaacgg catcactgct aacaaagaag   1320
tgtgcgaagg ttacgtttac aactctatcg gtatcgttac ttacctgaac ccgttcatcg   1380
gtcaccacaa cggtgacatc gtgggtaaaa tctgtgccga aaccggtaag agtgtacgtg   1440
aagtcgttct ggaacgcggt ctgttgactg aagcggaact tgacgatatt ttctccgtac   1500
agaatctgat gcacccggct tacaaagcaa aacgctatac tgatgaaagc gaacagtaat   1560
cgtacagggt agtacaaata aaaaaggcac gtcagatgac gtgccttttt tcttgtgagc   1620
ag                                                                  1622
```

<210> SEQ ID NO 7
<211> LENGTH: 2984
<212> TYPE: DNA
<213> ORGANISM: Escherichia coli

<400> SEQUENCE: 7

```
cgacctacac ctttggtgtt acttggggcg attttttaac atttccataa gttacgctta     60
tttaaagcgt cgtgaattta atgacgtaaa ttcctgctat ttattcgttt gctgaagcga    120
tttcgcagca tttgacgtca ccgcttttac gtggctttat aaaagacgac gaaaagcaaa    180
gcccgagcat attcgcgcca atgcgacgtg aaggatacag ggctatcaaa cgataagatg    240
gggtgtctgg ggtaatatga acgaacaata ttccgcattg cgtagtaatg tcagtatgct    300
cggcaaagtg ctgggagaaa ccatcaagga tgcgttggga gaacacattc ttgaacgcgt    360
```

```
agaaactatc cgtaagttgt cgaaatcttc acgcgctggc aatgatgcta accgccagga    420
gttgctcacc accttacaaa atttgtcgaa cgacgagctg ctgcccgttg cgcgtgcgtt    480
tagtcagttc ctgaacctgg ccaacaccgc cgagcaatac cacagcattt cgccgaaagg    540
cgaagctgcc agcaacccgg aagtgatcgc ccgcaccctg cgtaaactga aaaaccagcc    600
ggaactgagc gaagacacca tcaaaaaagc agtggaatcg ctgtcgctgg aactggtcct    660
cacggctcac ccaaccgaaa ttacccgtcg tacactgatc cacaaaatgg tggaagtgaa    720
cgcctgttta aaacagctcg ataacaaaga tatcgctgac tacgaacaca accagctgat    780
gcgtcgcctg cgccagttga tcgcccagtc atggcatacc gatgaaatcc gtaagctgcg    840
tccaagcccg gtagatgaag ccaaatgggg ctttgccgta gtggaaaaca gcctgtggca    900
aggcgtacca aattacctgc gcgaactgaa cgaacaactg gaagagaacc tcggctacaa    960
actgcccgtc gaatttgttc cggtccgttt tacttcgtgg atgggcggcg accgcgacgg   1020
caacccgaac gtcactgccg atatcacccg ccacgtcctg ctactcagcc gctggaaagc   1080
caccgatttg ttcctgaaag atattcaggt gctggtttct gaactgtcga tggttgaagc   1140 gaccccctgaa ctgctggcgc tggttggcga agaaggtgcc gcagaaccgt atcgctatct   1200
gatgaaaaac ctgcgttctc gcctgatggc gacacaggca tggctggaag cgcgcctgaa   1260
aggcgaagaa ctgccaaaac cagaaggcct gctgacacaa aacgaagaac tgtgggaacc   1320
gctctacgct tgctaccagt cacttcaggc gtgtggcatg gtattatcg ccaacggcga   1380 tctgctcgac accctgcgcc gcgtgaaatg tttcggcgta ccgctggtcc gtattgatat   1440
ccgtcaggag agcacgcgtc ataccgaagc gctgggcgag ctgacccgct acctcggtat   1500
cggcgactac gaaagctggt cagaggccga caaacaggcg ttcctgatcc gcgaactgaa   1560
ctccaaacgt ccgcttctgc cgcgcaactg gcaaccaagc gccgaaacgc gcgaagtgct   1620
cgatacctgc caggtgattg ccgaagcacc gcaaggctcc attgccgcct acgtgatctc   1680
gatggcgaaa acgccgtccg acgtactggc tgtccacctg ctgctgaaag aagcgggtat   1740 cgggttttgcg atgccggttg ctccgctgtt tgaaaccctc gatgatctga caacgccaa   1800 cgatgtcatg acccagctgc tcaatattga ctggtatcgt ggcctgattc agggcaaaca   1860
gatggtgatg attggctatt ccgactcagc aaaagatgcg ggagtgatgg cagcttcctg   1920
ggcgcaatat caggcacagg atgcattaat caaaacctgc gaaaaagcgg gtattgagct   1980
gacgttgttc cacggtcgcg gcggttccat tggtcgcggc ggcgcacctg ctcatgcggc   2040
gctgctgtca caaccgccag gaagcctgaa aggcggcctg cgcgtaaccg aacagggcga   2100
gatgatccgc tttaaatatg gtctgccaga aatcaccgtc agcagcctgt cgctttatac   2160
cggggcgatt ctggaagcca acctgctgcc accgccggag ccgaaagaga ctggcgtcg   2220 cattatggat gaactgtcag tcatctcctg cgatgtctac cgcggctacg tacgtgaaaa   2280
caaagatttt gtgccttact cccgctccgc tacgccggaa caagaactgg gcaaactgcc   2340
gttgggttca cgtccggcga acgtcgccc aaccggcggc gtcgagtcac tacgcgccat   2400
tccgtggatc ttcgcctgga cgcaaaaccg tctgatgctc cccgcctggc tgggtgcagg   2460
tacggcgctg caaaaagtgg tcgaagacgg caaacagagc gagctggagg ctatgtgccg   2520
cgattggcca ttcttctcga cgcgtctcgg catgctggag atggtcttcg ccaaagcaga   2580
cctgtggctg gcgaatact atgaccaacg cctggtagac aaagcactgt ggccgttagg   2640
taaagagtta cgcaaccctg caagaagaaga catcaaagtg gtgctggcga ttgccaacga   2700
```

| | |
|---|---|
| ttcccatctg atggccgatc tgccgtggat tgcagagtct attcagctac ggaatattta | 2760 |
| caccgacccg ctgaacgtat tgcaggccga gttgctgcac cgctcccgcc aggcagaaaa | 2820 |
| agaaggccag gaaccggatc ctcgcgtcga acaagcgtta atggtcacta ttgccgggat | 2880 |
| tgcggcaggt atgcgtaata ccggctaatc ttcctcttct gcaaaccctc gtgcttttgc | 2940 |
| gcgagggttt tctgaaatac ttctgttcta acaccctcgt tttc | 2984 |

<210> SEQ ID NO 8
<211> LENGTH: 1366
<212> TYPE: DNA
<213> ORGANISM: Escherichia coli

<400> SEQUENCE: 8

| | |
|---|---|
| ctttctgcgt gctaacaaag caggataagt cgcattactg atggcttcgc tatcattgat | 60 |
| taatttcact tgcgactttg gctgcttttt gtatggtgaa agatgtgcca agaggagacc | 120 |
| ggcacattta tacagcacac atctttgcag gaaaaaaacg cttatgaaaa atgttggttt | 180 |
| tatcggctgg cgcggtatgg tcggctccgt tctcatgcaa cgcatggttg aagagcgcga | 240 |
| cttcgacgcc attcgccctg tcttcttttc tacttctcag cttggccagg ctgcgccgtc | 300 |
| ttttggcgga accactggca cacttcagga tgcctttgat ctggaggcgc taaaggccct | 360 |
| cgatatcatt gtgacctgtc agggcggcga ttataccaac gaaatctatc aaagcttcg | 420 |
| tgaaagcgga tggcaaggtt actggattga cgcagcatcg tctctgcgca tgaaagatga | 480 |
| cgccatcatc attcttgacc ccgtcaatca ggacgtcatt accgacggat aaataatgg | 540 |
| catcaggact tttgttggcg gtaactgtac cgtaagcctg atgttgatgt cgttgggtgg | 600 |
| tttattcgcc aatgatcttg ttgattgggt gtccgttgca acctaccagg ccgcttccgg | 660 |
| cggtggtgcg cgacatatgc gtgagttatt aacccagatg ggccatctgt atggccatgt | 720 |
| ggcagatgaa ctcgcgaccc cgtcctctgc tattctcgat atcgaacgca agtcacaac | 780 |
| cttaacccgt agcggtgagc tgccggtgga taacttggc gtgccgctgg cgggtagcct | 840 |
| gattccgtgg atcgacaaac agctcgataa cggtcagagc cgcgaagagt ggaaagggca | 900 |
| ggcggaaacc aacaagatcc tcaacacatc ttccgtaatt ccggtagatg gtttatgtgt | 960 |
| gcgtgtcggg gcattgcgct gccacagcca ggcattcact attaaattga aaaagatgt | 1020 |
| gtctattccg accgtggaag aactgctggc tgcgcacaat ccgtgggcga agtcgttcc | 1080 |
| gaacgatcgg gaaatcacta tgcgtgagct aaccccagct gccgttaccg gcacgctgac | 1140 |
| cacgccggta ggccgcctgc gtaagctgaa tatgggacca gagttcctgt cagcctttac | 1200 |
| cgtgggcgac cagctgctgt gggggccgc ggagccgctg cgtcggatgc ttcgtcaact | 1260 |
| ggcgtaatct ttattcatta aatctggggc gcgatgccgc ccctgttagt gcgtaataca | 1320 |
| ggagtaagcg cagatgtttc atgatttacc gggagttaaa tagagc | 1366 |

<210> SEQ ID NO 9
<211> LENGTH: 3276
<212> TYPE: DNA
<213> ORGANISM: Escherichia coli

<400> SEQUENCE: 9

| | |
|---|---|
| ccactatcac ggctgaatcg ttaatatttt gcgagttcac gccgaaatac tgattttttgg | 60 |
| cgctagatca caggcataat tttcagtacg ttatagggcg tttgttacta atttatttta | 120 |
| acggagtaac atttagctcg tacatgagca gcttgtgtgg ctcctgacac aggcaaacca | 180 |
| tcatcaataa aaccgatgga agggaatatc atgcgaattg cataccaag agaacggtta | 240 |

```
accaatgaaa cccgtgttgc agcaacgcca aaaacagtgg aacagctgct gaaactgggt    300
tttaccgtcg cggtagagag cggcgcgggt caactggcaa gttttgacga taaagcgttt    360
gtgcaagcgg gcgctgaaat tgtagaaggg aatagcgtct ggcagtcaga gatcattctg    420
aaggtcaatg cgccgttaga tgatgaaatt gcgttactga atcctgggac aacgctggtg    480
agttttatct ggcctgcgca gaatccggaa ttaatgcaaa aacttgcgga acgtaacgtg    540
accgtgatgg cgatggactc tgtgccgcgt atctcacgcg cacaatcgct ggacgcacta    600
agctcgatgg cgaacatcgc cggttatcgc gccattgttg aagcggcaca tgaatttggg    660
cgcttcttta ccgggcaaat tactgcgccc gggaaagtgc caccggcaaa agtgatggtg    720
attggtgcgg gtgttgcagg tctggccgcc attggcgcag caaacagtct cggcgcgatt    780
gtgcgtgcat tcgacacccg cccggaagtg aaagaacaag ttcaaagtat gggcgcggaa    840
ttcctcgagc tggattttaa agaggaagct ggcagcggcg atggctatgc caaagtgatg    900
tcggacgcgt tcatcaaagc ggaaatggaa ctctttgccg cccaggcaaa agaggtcgat    960
atcattgtca ccaccgcgct tattccaggc aaaccagcgc cgaagctaat tacccgtgaa   1020
atggttgact ccatgaaggc gggcagtgtg attgtcgacc tggcagccca aaacggcggc   1080
aactgtgaat acaccgtgcc gggtgaaatc ttcactacgg aaaatggtgt caaagtgatt   1140
ggttataccg atcttccggg ccgtctgccg acgcaatcct cacagcttta cggcacaaac   1200
ctcgttaatc tgctgaaact gttgtgcaaa gagaaagacg gcaatatcac tgttgatttt   1260
gatgatgtgg tgattcgcgg cgtgaccgtg atccgtgcgg gcgaaattac ctggccggca   1320
ccgccgattc aggtatcagc tcagccgcag gcggcacaaa aagcggcacc ggaagtgaaa   1380
actgaggaaa aatgtacctg ctcaccgtgg cgtaaatacg cgttgatggc gctggcaatc   1440
attctttttg gctggatggc aagcgttgcg ccgaaagaat tccttgggca cttcaccgtt   1500
ttcgcgctgg cctgcgttgt cggttattac gtggtgtgga atgtatcgca cgcgctgcat   1560
acaccgttga tgtcggtcac caacgcgatt tcagggatta ttgttgtcgg agcactgttg   1620
cagattggcc agggcggctg ggttagcttc cttagtttta tcgcggtgct tatagccagc   1680
attaatattt tcggtggctt caccgtgact cagcgcatgc tgaaaatgtt ccgcaaaaat   1740 taagggtaa catatgtctg gaggattagt tacagctgca tacattgttg ccgcgatcct   1800
gtttatcttc agtctggccg gtctttcgaa acatgaaacg tctcgccagg gtaacaactt   1860
cggtatcgcc gggatggcga ttgcgttaat cgcaaccatt tttggaccgg atacgggtaa   1920
tgttggctga tcttgctgg cgatggtcat tggtggggca attggtatcc gtctggcgaa   1980
gaaagttgaa atgaccgaaa tgccagaact ggtggcgatc ctgcatagct tcgtgggtct   2040
ggcggcagtg ctggttggct ttaacagcta tctgcatcat gacgcgggaa tggcaccgat   2100
tctggtcaat attcacctga cggaagtgtt cctcggtatc ttcatcgggg cggtaacgtt   2160
cacgggttcg gtggtggcgt tcggcaaact gtgtggcaag atttcgtcta aaccattgat   2220
gctgccaaac cgtcacaaaa tgaacctggc ggctctggtc gtttccttcc tgctgctgat   2280
tgtatttgtt cgcacggaca gcgtcggcct gcaagtgctg gcattgctga taatgaccgc   2340
aattgcgctg tattcggct ggcatttagt cgcctccatc ggtggtgcag atatgccagt   2400
ggtggtgtcg atgctgaact cgtactccgg ctgggcggct gcggctgcgg ctttatgct   2460 cagcaacgac ctgctgattg tgaccggtgc gctggtcggt tcttcggggg ctatcctttc   2520
ttacattatg tgtaaggcga tgaaccgttc ctttatcagc gttattgcgg gtggtttcgg   2580
```

```
caccgacggc tcttctactg gcgatgatca ggaagtgggt gagcaccgcg aaatcaccgc   2640
agaagagaca gcggaactgc tgaaaaactc ccattcagtg atcattactc cggggtacgg   2700
catggcagtc gcgcaggcgc aatatcctgt cgctgaaatt actgagaaat tgcgcgctcg   2760
tggtattaat gtgcgtttcg gtatccaccc ggtcgcgggg cgtttgcctg acatatgaa    2820 cgtattgctg gctgaagcaa agtaccgta tgacatcgtg ctggaaatgg acgagatcaa    2880
tgatgacttt gctgataccg ataccgtact ggtgattggt gctaacgata cggttaaccc    2940
ggcggcgcag gatgatccga agagtccgat tgctggtatg cctgtgctgg aagtgtggaa    3000
agcgcagaac gtgattgtct ttaaacgttc gatgaacact ggctatgctg gtgtgcaaaa    3060
cccgctgttc ttcaaggaaa acacccacat gctgtttggt gacgccaaag ccagcgtgga    3120
tgcaatcctg aaagctctgt aaccctgacg gcctctgctg aggccgtcac tctttattga    3180
gatcgcttaa cagaacggcg atgctttgac ctcccgctgt ttgttcaagc gcaattttga    3240
caataattgt caacggcacg gaaagcagca taccca                              3276
```

<210> SEQ ID NO 10
<211> LENGTH: 162
<212> TYPE: DNA
<213> ORGANISM: Escherichia coli

<400> SEQUENCE: 10

```
caattccgac gtctaagaag ccattactat catgacatta acctatagga ataggcgtat    60
cacggggccc ttccgccttc acctcggatc cctgtcagtg ctagagattg acatccctac   120
cggtgataaa gatactgagc acatcagcag gacgcactga cc                      162
```

<210> SEQ ID NO 11
<211> LENGTH: 88
<212> TYPE: DNA
<213> ORGANISM: Escherichia coli

<400> SEQUENCE: 11

```
gggcccaagt tcacttaaaa aggagatcaa caatgaaagc aattttcgta ctgaaacatc    60
ttaatcatgc acaggagact ttctaatg                                       88
```

<210> SEQ ID NO 12
<211> LENGTH: 1097
<212> TYPE: DNA
<213> ORGANISM: Escherichia coli

<400> SEQUENCE: 12

```
aaaggatgcc tggttcatta cgtaaaatgc cggtctggtt accaatagtc atattgctcg    60
ttgccatggc gtctattcag ggtggagcct cgttagctaa gtcactttt cctctggtgg    120 gcgcaccggg tgtcactgcg ctgcgtctgg cattaggaac gctgatcctc atcgcgttct   180
ttaagccatg gcgactgcgc tttgccaaag agcaacggtt accgctgttg ttttacggcg   240
tttcgctggg tgggatgaat tatctttttt atctttctat tcagacagta ccgctgggta   300
ttgcggtggc gctggagttc accggaccac tggcggtggc gctgttctct tctcgtcgcc   360
cggtagattt cgtctgggtt gtgctggcgg ttcttggtct gtggttcctg ctaccgctgg   420
ggcaagacgt ttcccatgtc gatttaaccg gctgtgcgct ggcactgggg gccggggctt   480
gttgggctat ttcacttta agtgggcaac gcgcaggagc ggaacatggc cctgcgacgg   540
tgcaattgtt ttcgttgatt gcagcgttaa ttttcgtgcc aattggagcg cttcaggctg   600
gtgaagcact ctggcactgg tcggttattc cattgggtct ggctgtcgct attctctcga   660
```

```
ccgctctgcc ttattcgctg gaaatgattg ccctcacccg tttgccaaca cggacatttg    720
gtacgctgat gagcatggaa ccggcgctgg ctgccgtttc cgggatgatt ttcctcggag    780
aaacactgac acccatacag ctactggcgc tcggcgctat catcgccgct tcaatggggt    840
ctacgctgac agtacgcaaa gagagcaaaa taaaagaatt agacattaat taaatttaca    900
tttctgcatg gttatgcata accatgcaga atttctcgct acttttcctc tacaccgtct    960
ttatatatcg aattatgcaa aagcatattt attccgaaaa ttcctggcga gcagataaat   1020
aagaattgtt cttatcaata tatctaactc attgaatctt tattagtttt gttttttcacg   1080 cttgttacca ctattag                                                  1097

<210> SEQ ID NO 13
<211> LENGTH: 825
<212> TYPE: DNA
<213> ORGANISM: Escherichia coli

<400> SEQUENCE: 13
tcatcatgac cttagaatgg tggtttgcct acctgctgac atcgatcatt ttaagcctgt     60
cgccaggctc tggtgcaatc aacactatga ccacctcgct caaccacggt tatcgcggcg    120
cggtggcgtc tattgctggg cttcagaccg gactggcgat tcatattgtg ctggttggcg    180
tggggttggg gacgctattt tcccgctcag tgattgcgtt tgaagtgttg aagtgggcag    240
gcgcggctta cttgatttgg ctgggaatcc agcagtggcg cgccgctggt gcaattgacc    300
ttaaatcgct ggcctctact caatcgcgtc gacatttgtt ccagcgcgca gtttttgtga    360
atctcaccaa tcccaaaagt attgtgtttc tggcggcgct atttccgcaa ttcatcatgc    420
cgcaacagcc gcaactgatg cagtatatcg tgctcggcgt caccactatt gtggtcgata    480
ttattgtgat gatcggttac gccacccttg ctcaacggat tgctctatgg attaaaggac    540
caaagcagat gaaggcgctg aataagattt tcggctcgtt gtttatgctg gtgggagcgc    600
tgttagcatc ggcgaggcat gcgtgaaaaa taatgtcgga tgcggcgtaa acgccttatc    660
cgacttactc tgaagacgcg tctggcatca ccgcgaaata atcaaatgaa tgccaaatcc    720
ggcaaataac gccccggcaa aaccatcaat ccacttcgcc agacgttgat aaccacggcg    780
catttgcggc agggcaaaca ggctggcaac gacggtaaac cacgc                   825

<210> SEQ ID NO 14
<211> LENGTH: 807
<212> TYPE: DNA
<213> ORGANISM: Escherichia coli

<400> SEQUENCE: 14
aatgtatgtt gatgttattt ctcaccgtcg ccatggtgca cattgtggcg cttatgagcc     60
ccggtcccga tttctttttt gtctctcaga ccgctgtcag tcgttcccgt aaagaagcga    120
tgatgggcgt gctgggcatt acctgcgcg taatggtttg gctgggatt gcgctgcttg    180 gcctgcattt gattatcgaa aaaatggcct ggctgcatac gctgattatg gtgggcggtg    240
gcctgtatct ctgctggatg ggttaccaga tgctacgtgg tgcactgaaa aagaggcgg    300 tttctgcacc tgcgccacag gtcgagctgg cgaaaagtgg gcgcagtttc ctgaaaggtt    360
tactgaccaa tctcgctaat ccgaaagcga ttatctactt tggctcggtg ttctcattgt    420
ttgtcggtga taacgttggc actaccgcgc gctggggcat ttttgcgctg atcattgtcg    480
aaacgctggc gtggtttacc gtcgttgcca gcctgtttgc cctgccgcaa atgcgccgtg    540
```

| | | |
|---|---|---|
| gttatcaacg tctggcgaag tggattgatg gttttgccgg ggcgttattt gccggatttg | 600 | |
| gcattcattt gattatttcg cggtgatgcc agacgcgtct tcagagtaag tcggataagg | 660 | |
| cgtttacgcc gcatccgaca ttattttca cgcatgcctc gccgatgcta acagcgctcc | 720 | |
| caccagcata acaacgagc cgaaaatctt attcagcgcc ttcatctgct ttggtccttt | 780 | |
| aatccataga gcaatccgtt gagcaag | 807 | |

<210> SEQ ID NO 15
<211> LENGTH: 846
<212> TYPE: DNA
<213> ORGANISM: Escherichia coli

<400> SEQUENCE: 15

| | | |
|---|---|---|
| ccaaaatgag tgccattgaa gttaagaacc tggtgaaaaa attccacggt cagacggtgc | 60 | |
| tgcacggtat cgaccttgag gtaaagcctg gcgaagtggt ggcaattatc ggtccgagtg | 120 | |
| gttccggcaa aaccacgttg ctacgcagca taaatctgct ggaacaaccc gaagcgggaa | 180 | |
| cgatcaccgt tggcgatatc actattgata ctgcacgttc attaagtcag caaaaatctc | 240 | |
| tgattcgcca gttgcgtcag cacgtcgggt ttgtcttcca gaactttaat ttgtttccgc | 300 | |
| atcgtacggt gctggagaac attattgaag gccggtgat cgtcaaaggt gaaccgaaag | 360 | |
| aagaggccac ggcgcgcgct cgcgagctgc tggcaaaagt tgggctggca ggtaaagaaa | 420 | |
| ccagctatcc acgtcgtttg tctggcggtc aacagcagcg tgttgcgatt gcgcgtgcgc | 480 | |
| tggcaatgcg tcctgaggtg attttgtttg acgagccaac gtcagcgctg atccagagc | 540 | |
| tggtgggtga agtcctgaac accatccgtc agctggcgca ggaaaagcgc acgatggtga | 600 | |
| ttgtgacgca cgaaatgagc tttgcccggg atgttgcgga ccgggcgatc tttatggacc | 660 | |
| aggggcggat agtcgagcag ggggccgcaa aagcgttatt tgccgacccc gagcagcctc | 720 | |
| gcacccgcca gttcctcgag aagtttctgc tgcaataata gaaaaaatc agccccgacg | 780 | |
| attcacctgt cggggctgga cgccatttca agcctgataa aactgcttaa caaatcagca | 840 | |
| taactc | 846 | |

<210> SEQ ID NO 16
<211> LENGTH: 2350
<212> TYPE: DNA
<213> ORGANISM: Escherichia coli

<400> SEQUENCE: 16

| | | |
|---|---|---|
| ggatgcagga aatgctctac ccaaccagct tcctgaaatc aatgggtctc ggcaaagcct | 60 | |
| gtgcgctgat caccgacggt cgtttctctg gtggcacctc tggtctttcc atcggccacg | 120 | |
| tctcaccgga agcggcaagc ggcggcagca ttggcctgat tgaagatggt gacctgatcg | 180 | |
| ctatcgacat cccgaaccgt ggcattcagt tacaggtaag cgatgccgaa ctggcggcgc | 240 | |
| gtcgtgaagc gcaggacgct cgaggtgaca aagcctggac gccgaaaaat cgtgaacgtc | 300 | |
| aggtctcctt tgccctgcgt gcttatgcca gcctggcaac cagcgccgac aaaggcgcgg | 360 | |
| tgcgcgataa atcgaaactg gggggttaat aatggctgac tcgcaacccc tgtccggtgc | 420 | |
| tccggaaggt gccgaatatt taagagcagt gctgcgcgcg ccggtttacg aggcggcgca | 480 | |
| ggttacgccg ctacaaaaaa tggaaaaact gtcgtcgcgt cttgataacg tcattctggt | 540 | |
| gaagcgcgaa gatcgccagc cagtgcacag ctttaagctg cgcggcgcat acgccatgat | 600 | |
| ggcggggcctg acgaagaac agaaagcgca cggcgtgatc actgcttctg cgggtaacca | 660 | |
| cgcgcagggc gtcgcgtttt cttctgcgcg gttaggcgtg aaggcctga tcgttatgcc | 720 | |

-continued

| | |
|---|---|
| aaccgccacc gccgacatca aagtcgacgc ggtgcgcggc ttcggcggcg aagtgctgct | 780 |
| ccacggcgcg aactttgatg aagcgaaagc caaagcgatc gaactgtcac agcagcaggg | 840 |
| gttcacctgg gtgccgccgt tcgaccatcc gatggtgatt gccgggcaag gcacgctggc | 900 |
| gctggaactg ctccagcagg acgcccatct cgaccgcgta tttgtgccag tcggcggcgg | 960 |
| cggtctggct gctggcgtgg cggtgctgat caaacaactg atgccgcaaa tcaaagtgat | 1020 |
| cgccgtagaa gcgaagact ccgcctgcct gaaagcagcg ctggatgcgg gtcatccggt | 1080 |
| tgatctgccg cgcgtagggc tatttgctga aggcgtagcg gtaaaacgca tcggtgacga | 1140 |
| aaccttccgt ttatgccagg agtatctcga cgacatcatc accgtcgata gcgatgcgat | 1200 |
| ctgtgcggcg atgaaggatt tattcgaaga tgtgcgcgcg gtggcggaac cctctggcgc | 1260 |
| gctggcgctg gcgggaatga aaaaatatat cgccctgcac aacattcgcg gcgaacggct | 1320 |
| ggcgcatatt ctttccggtg ccaacgtgaa cttccacggc ctgcgctacg tctcagaacg | 1380 |
| ctgcgaactg ggcgaacagc gtgaagcgtt gttggcggtg accattccgg aagaaaaagg | 1440 |
| cagcttcctc aaattctgcc aactgcttgg cgggcgttcg gtcaccgagt tcaactaccg | 1500 |
| ttttgccgat gccaaaaacg cctgcatctt tgtcggtgtg cgcctgagcc gcggcctcga | 1560 |
| agagcgcaaa gaattttgc agatgctcaa cgacggcggc tacagcgtgg ttgatctctc | 1620 |
| cgacgacgaa atggcgaagc tacacgtgcg ctatatggtc ggcggacgtc catcgcatcc | 1680 |
| gttgcaggaa cgcctctaca gcttcgaatt cccggaatca ccgggcgcgc tgctgcgctt | 1740 |
| cctcaacacg ctgggtacgt actggaacat ttctttgttc cactatcgca gccatggcac | 1800 |
| cgactacggg cgcgtactgg cggcgttcga acttggcgac catgaaccgg atttcgaaac | 1860 |
| ccggctgaat gagctgggct acgattgcca cgacgaaacc aataacccgg cgttcaggtt | 1920 |
| cttttttggcg ggttagggaa aaatgcctga tagcgcttcg cttatcaggc ctaccccgcgc | 1980 |
| gacaacgtca tttgtggttc ggcaaaatct tccagaatgc ctcaattagc ggctcatgta | 2040 |
| gccgctttt ctgcgcacac acgcccagct caaacggcgt tttctcatcg ctgcgctcta | 2100 |
| aaatcatcac gcggttacgc accggttcgg ggctgtttc cagcaccact tccggcaaca | 2160 |
| atgccacgcc acagccgagt gccaccatcg ataccatcgc ttcatgcccg ccaaccgtgg | 2220 |
| cgtaaatcat cgggttactg attttattgc gtcgaaacca cagttcaatg cggcggcgta | 2280 |
| ccggcccctg atcggccata ataaacggca ccgttgacca gtccggcttc tctaccgaca | 2340 |
| cctgattacg | 2350 |

<210> SEQ ID NO 17
<211> LENGTH: 1812
<212> TYPE: DNA
<213> ORGANISM: Escherichia coli

<400> SEQUENCE: 17

| | |
|---|---|
| tccgtacctg ttctccaact cgctggcacc ggccattgtt gccgcgtcca tcaaagtact | 60 |
| ggagatggtc gaagcgggca gcgaactgcg tgaccgtctg tgggcgaacg cgcgtcagtt | 120 |
| ccgtgagcaa atgtcggcgg cgggctttac cctggcggga gccgatcacg ccattattcc | 180 |
| ggtcatgctt ggtgatgcgg tagtggcgca gaaatttgcc cgtgagctgc aaaaagaggg | 240 |
| catttacgtt accggtttct tctatccggt cgttccgaaa ggtcaggcgc gtattcgtac | 300 |
| ccagatgtct gcgcgcata cccctgagca aattacgcgt gcagtagaag catttacgcg | 360 |
| tattggtaaa caactgggcg ttatcgcctg aggatgtgag atgaaagcgt tatccaaact | 420 |

```
gaaagcggaa gagggcatct ggatgaccga cgttcctgta ccggaactcg ggcataacga      480
tctgctgatt aaaatccgta aaacagccat ctgcgggact gacgttcaca tctataactg      540
ggatgagtgg tcgcaaaaaa ccatcccggt gccgatggtc gtgggccatg aatatgtcgg      600
tgaagtggta ggtattggtc aggaagtgaa aggcttcaag atcggcgatc gcgtttctgg      660
cgaaggccat atcacctgtg gtcattgccg caactgtcgt ggtggtcgta cccatttgtg      720
ccgcaacacg ataggcgttg gtgttaatcg cccgggctgc tttgccgaat atctggtgat      780
cccggcattc aacgccttca aaatccccga caatatttcc gatgacttag ccgcaatttt      840
tgatcccttc ggtaacgccg tgcataccgc gctgtcgttt gatctggtgg gcgaagatgt      900
gctggtttct ggtgcaggcc cgattggtat tatggcagcg gcggtggcga aacacgttgg      960
tgcacgcaat gtggtgatca ctgatgttaa cgaataccgc cttgagctgg cgcgtaaaat     1020
gggtatcacc cgtgcggtta acgtcgccaa agaaaatctc aatgacgtga tggcggagtt     1080
aggcatgacc gaaggttttg atgtcggtct ggaaatgtcc ggtgcgccgc cagcgtttcg     1140
taccatgctt gacaccatga atcacggcgg ccgtattgcg atgctgggta ttccgccgtc     1200
tgatatgtct atcgactgga ccaaagtgat ctttaaaggc ttgttcatta aaggtatttta    1260 cggtcgtgag atgtttgaaa cctggtacaa gatggcggcg ctgattcagt ctggcctcga     1320
tctttcgccg atcattaccc atcgtttctc tatcgatgat ttccagaagg gctttgacgc     1380
tatgcgttcg ggccagtccg ggaaagttat tctgagctgg gattaacacg aacaagggct     1440
ggtattccag ccctttttatc tgaggataat ctgttaaata tgtaaaatcc tgtcagtgta    1500
ataaagagtt cgtaattgtg ctgatctctt atatagctgc tctcattatc tctctacccct    1560 gaagtgactc tctcacctgt aaaaataata tctcacaggc ttaatagttt cttaatacaa     1620
agcctgtaaa acgtcaggat aacttcagag gtcgtcggta atttatgatg aacagcacca     1680
ataaacttag tgttattatt ccgttatata atgcgggcga tgatttccgc acttgtatgg     1740
aatctttaat tacgcaaacc tggactgctc tggaaatcat tattattaac gatggttcaa     1800
cggataattc tg                                                         1812
```

<210> SEQ ID NO 18
<211> LENGTH: 11
<212> TYPE: DNA
<213> ORGANISM: Artificial Sequence
<220> FEATURE:
<223> OTHER INFORMATION: Type IIS RE recognition site with single-base
      sticky ends
<220> FEATURE:
<221> NAME/KEY: misc_feature
<222> LOCATION: (7)..(11)
<223> OTHER INFORMATION: n is a, c, g, or t

<400> SEQUENCE: 18
actgggnnnn n                                                            11

<210> SEQ ID NO 19
<211> LENGTH: 10
<212> TYPE: DNA
<213> ORGANISM: Artificial Sequence
<220> FEATURE:
<223> OTHER INFORMATION: Type IIS RE recognition site with blunt ends
<220> FEATURE:
<221> NAME/KEY: misc_feature
<222> LOCATION: (6)..(10)
<223> OTHER INFORMATION: n is a, c, g, or t

<400> SEQUENCE: 19

-continued

```
gagtcnnnnn                                                           10

<210> SEQ ID NO 20
<211> LENGTH: 16
<212> TYPE: DNA
<213> ORGANISM: Artificial Sequence
<220> FEATURE:
<223> OTHER INFORMATION: position signals of mCherry gene

<400> SEQUENCE: 20
cctccccagt gcatgc                                                    16

<210> SEQ ID NO 21
<211> LENGTH: 22
<212> TYPE: DNA
<213> ORGANISM: Artificial Sequence
<220> FEATURE:
<223> OTHER INFORMATION: pTargetF-tdh

<400> SEQUENCE: 21
ccgtgcggtt aacgtcgcca aa                                             22

<210> SEQ ID NO 22
<211> LENGTH: 23
<212> TYPE: DNA
<213> ORGANISM: Artificial Sequence
<220> FEATURE:
<223> OTHER INFORMATION: pTargetF-ilvA

<400> SEQUENCE: 22
cttcatcaaa gttcgcgccg tgg                                            23

<210> SEQ ID NO 23
<211> LENGTH: 58
<212> TYPE: DNA
<213> ORGANISM: Artificial Sequence
<220> FEATURE:
<223> OTHER INFORMATION: primer UC709-F

<400> SEQUENCE: 23
tgcgtattgg gcgctcttcc gcttcctcgc tcactgacac gctgcgctcg gtcgttcg      58

<210> SEQ ID NO 24
<211> LENGTH: 43
<212> TYPE: DNA
<213> ORGANISM: Artificial Sequence
<220> FEATURE:
<223> OTHER INFORMATION: primer UC1179-R

<400> SEQUENCE: 24
gtcgtgtctt accgggttgg aatcaagacg atagttaccg gat                      43

<210> SEQ ID NO 25
<211> LENGTH: 43
<212> TYPE: DNA
<213> ORGANISM: Artificial Sequence
<220> FEATURE:
<223> OTHER INFORMATION: primer UC1179-f

<400> SEQUENCE: 25
atccggtaac tatcgtcttg attccaaccc ggtaagacac gac                      43

<210> SEQ ID NO 26
<211> LENGTH: 59
<212> TYPE: DNA
<213> ORGANISM: Artificial Sequence
```

```
<220> FEATURE:
<223> OTHER INFORMATION: primer UC1695-R

<400> SEQUENCE: 26
tggtaagccc tcccgtatcg tagttatcta cacgacgggg agccaggcaa ctatggatg      59

<210> SEQ ID NO 27
<211> LENGTH: 59
<212> TYPE: DNA
<213> ORGANISM: Artificial Sequence
<220> FEATURE:
<223> OTHER INFORMATION: primer UC1746-R

<400> SEQUENCE: 27
agcgtgggtc tcgcggtatc attgcagcac tagggccaga tggtaagccc tcccgtatc      59

<210> SEQ ID NO 28
<211> LENGTH: 43
<212> TYPE: DNA
<213> ORGANISM: Artificial Sequence
<220> FEATURE:
<223> OTHER INFORMATION: primer pUC19- MlyI1177-R

<400> SEQUENCE: 28
gtcgtgtctt accgggttgg aatcaagacg atagttaccg gat                       43

<210> SEQ ID NO 29
<211> LENGTH: 19
<212> TYPE: DNA
<213> ORGANISM: Artificial Sequence
<220> FEATURE:
<223> OTHER INFORMATION: primer UC1

<400> SEQUENCE: 29
gcacagatgc gtaaggaga                                                  19

<210> SEQ ID NO 30
<211> LENGTH: 21
<212> TYPE: DNA
<213> ORGANISM: Artificial Sequence
<220> FEATURE:
<223> OTHER INFORMATION: primer UC2

<400> SEQUENCE: 30
gcaggaaaga acatgtgagc a                                               21

<210> SEQ ID NO 31
<211> LENGTH: 20
<212> TYPE: DNA
<213> ORGANISM: Artificial Sequence
<220> FEATURE:
<223> OTHER INFORMATION: primer UC3

<400> SEQUENCE: 31
aggatcttca cctagatcct                                                 20

<210> SEQ ID NO 32
<211> LENGTH: 20
<212> TYPE: DNA
<213> ORGANISM: Artificial Sequence
<220> FEATURE:
<223> OTHER INFORMATION: UC4 primer

<400> SEQUENCE: 32
gttcgatgta acccactcgt                                                 20
```

<210> SEQ ID NO 33
<211> LENGTH: 34
<212> TYPE: DNA
<213> ORGANISM: Artificial Sequence
<220> FEATURE:
<223> OTHER INFORMATION: primer mC-F

<400> SEQUENCE: 33
gggaattcca tatgatggtg agcaagggcg agga                          34

<210> SEQ ID NO 34
<211> LENGTH: 38
<212> TYPE: DNA
<213> ORGANISM: Artificial Sequence
<220> FEATURE:
<223> OTHER INFORMATION: primer mCB-R

<400> SEQUENCE: 34
acatgcatgc actggggagg agtcctgggt cacggtca                      38

<210> SEQ ID NO 35
<211> LENGTH: 37
<212> TYPE: DNA
<213> ORGANISM: Artificial Sequence
<220> FEATURE:
<223> OTHER INFORMATION: primer mCM-R

<400> SEQUENCE: 35
acatgcatgc gagtcgagta gtcctgggtc acggtca                       37

<210> SEQ ID NO 36
<211> LENGTH: 21
<212> TYPE: DNA
<213> ORGANISM: Artificial Sequence
<220> FEATURE:
<223> OTHER INFORMATION: primer FB-F

<400> SEQUENCE: 36
cctccctgca ggacggcgag t                                        21

<210> SEQ ID NO 37
<211> LENGTH: 36
<212> TYPE: DNA
<213> ORGANISM: Artificial Sequence
<220> FEATURE:
<223> OTHER INFORMATION: primer FB-R

<400> SEQUENCE: 37
acatgcatgc actgggttac ttgtacagct cgtcca                        36

<210> SEQ ID NO 38
<211> LENGTH: 22
<212> TYPE: DNA
<213> ORGANISM: Artificial Sequence
<220> FEATURE:
<223> OTHER INFORMATION: primer FM-F

<400> SEQUENCE: 38
tcctccctgc aggacggcga gt                                       22

<210> SEQ ID NO 39
<211> LENGTH: 35
<212> TYPE: DNA
<213> ORGANISM: Artificial Sequence
<220> FEATURE:
<223> OTHER INFORMATION: primer FM-R

<400> SEQUENCE: 39
acatgcatgc gagtcttact tgtacagctc gtcca                              35

<210> SEQ ID NO 40
<211> LENGTH: 21
<212> TYPE: DNA
<213> ORGANISM: Artificial Sequence
<220> FEATURE:
<223> OTHER INFORMATION: primer UC5

<400> SEQUENCE: 40
acggtgaaaa cctctgacac a                                             21

<210> SEQ ID NO 41
<211> LENGTH: 21
<212> TYPE: DNA
<213> ORGANISM: Artificial Sequence
<220> FEATURE:
<223> OTHER INFORMATION: primer UC6

<400> SEQUENCE: 41
cgcaacgcaa ttaatgtgag t                                             21

<210> SEQ ID NO 42
<211> LENGTH: 43
<212> TYPE: DNA
<213> ORGANISM: Artificial Sequence
<220> FEATURE:
<223> OTHER INFORMATION: primer AC3211-F

<400> SEQUENCE: 42
accacgatac tatgactgag tgtcaacgcc atgagcggcc tca                     43

<210> SEQ ID NO 43
<211> LENGTH: 36
<212> TYPE: DNA
<213> ORGANISM: Artificial Sequence
<220> FEATURE:
<223> OTHER INFORMATION: primer AC727-R

<400> SEQUENCE: 43
gaacgaccga gcgtagcgtg tcagtgagcg aggaag                             36

<210> SEQ ID NO 44
<211> LENGTH: 36
<212> TYPE: DNA
<213> ORGANISM: Artificial Sequence
<220> FEATURE:
<223> OTHER INFORMATION: primer AC727-F

<400> SEQUENCE: 44
cttcctcgct cactgacacg ctacgctcgg tcgttc                             36

<210> SEQ ID NO 45
<211> LENGTH: 59
<212> TYPE: DNA
<213> ORGANISM: Artificial Sequence
<220> FEATURE:
<223> OTHER INFORMATION: primer AC1143-R

<400> SEQUENCE: 45
agtggtgctt ttgcatgtct ttccggttg gaatcaagac gatagttacc ggataaggc     59

<210> SEQ ID NO 46

<211> LENGTH: 40
<212> TYPE: DNA
<213> ORGANISM: Artificial Sequence
<220> FEATURE:
<223> OTHER INFORMATION: primer TAB-F

<400> SEQUENCE: 46
cccaagcttg agtcagggat cttctgaacg ctcaatctct                40

<210> SEQ ID NO 47
<211> LENGTH: 49
<212> TYPE: DNA
<213> ORGANISM: Artificial Sequence
<220> FEATURE:
<223> OTHER INFORMATION: primer TAB-R

<400> SEQUENCE: 47
ggcataaact ttaaccatgt caaactccta acttccatga gagggtacg            49

<210> SEQ ID NO 48
<211> LENGTH: 49
<212> TYPE: DNA
<213> ORGANISM: Artificial Sequence
<220> FEATURE:
<223> OTHER INFORMATION: primer TBC-F

<400> SEQUENCE: 48
cgtaccctct catggaagtt aggagtttga catggttaaa gtttatgcc            49

<210> SEQ ID NO 49
<211> LENGTH: 54
<212> TYPE: DNA
<213> ORGANISM: Artificial Sequence
<220> FEATURE:
<223> OTHER INFORMATION: primer TBC-R

<400> SEQUENCE: 49
gctcacgtcc atcgcgttgg ataacgtcgc ctgcgtcgct ttgggtgacc actg          54

<210> SEQ ID NO 50
<211> LENGTH: 50
<212> TYPE: DNA
<213> ORGANISM: Artificial Sequence
<220> FEATURE:
<223> OTHER INFORMATION: primer TC-F

<400> SEQUENCE: 50
gcaggcgacg ttatccaacg cgatggacgt gagccagccg aacaactggc           50

<210> SEQ ID NO 51
<211> LENGTH: 30
<212> TYPE: DNA
<213> ORGANISM: Artificial Sequence
<220> FEATURE:
<223> OTHER INFORMATION: primer TC-R

<400> SEQUENCE: 51
ccctcgcgag catttattga gaatttctcc                  30

<210> SEQ ID NO 52
<211> LENGTH: 34
<212> TYPE: DNA
<213> ORGANISM: Artificial Sequence
<220> FEATURE:
<223> OTHER INFORMATION: primer TA-F

<400> SEQUENCE: 52
cccaagcttg agtcctggtc gactggttac aaca                                34

<210> SEQ ID NO 53
<211> LENGTH: 23
<212> TYPE: DNA
<213> ORGANISM: Artificial Sequence
<220> FEATURE:
<223> OTHER INFORMATION: primer TAphe-R

<400> SEQUENCE: 53
aaactgagca atggcgacaa tgt                                            23

<210> SEQ ID NO 54
<211> LENGTH: 23
<212> TYPE: DNA
<213> ORGANISM: Artificial Sequence
<220> FEATURE:
<223> OTHER INFORMATION: primer TALeu-R

<400> SEQUENCE: 54
cagctgagca atggcgacaa tgt                                            23

<210> SEQ ID NO 55
<211> LENGTH: 23
<212> TYPE: DNA
<213> ORGANISM: Artificial Sequence
<220> FEATURE:
<223> OTHER INFORMATION: primer TAIle-R

<400> SEQUENCE: 55
aatctgagca atggcgacaa tgt                                            23

<210> SEQ ID NO 56
<211> LENGTH: 23
<212> TYPE: DNA
<213> ORGANISM: Artificial Sequence
<220> FEATURE:
<223> OTHER INFORMATION: primer TAMet-R

<400> SEQUENCE: 56
catctgagca atggcgacaa tgt                                            23

<210> SEQ ID NO 57
<211> LENGTH: 23
<212> TYPE: DNA
<213> ORGANISM: Artificial Sequence
<220> FEATURE:
<223> OTHER INFORMATION: primer TAVal-R

<400> SEQUENCE: 57
cacctgagca atggcgacaa tgt                                            23

<210> SEQ ID NO 58
<211> LENGTH: 23
<212> TYPE: DNA
<213> ORGANISM: Artificial Sequence
<220> FEATURE:
<223> OTHER INFORMATION: primer TASer-R

<400> SEQUENCE: 58
gctctgagca atggcgacaa tgt                                            23

<210> SEQ ID NO 59
<211> LENGTH: 23
<212> TYPE: DNA

```
<213> ORGANISM: Artificial Sequence
<220> FEATURE:
<223> OTHER INFORMATION: primer TAPro-R

<400> SEQUENCE: 59
cggctgagca atggcgacaa tgt                                              23

<210> SEQ ID NO 60
<211> LENGTH: 23
<212> TYPE: DNA
<213> ORGANISM: Artificial Sequence
<220> FEATURE:
<223> OTHER INFORMATION: primer TAThr-R

<400> SEQUENCE: 60
ggtctgagca atggcgacaa tgt                                              23

<210> SEQ ID NO 61
<211> LENGTH: 23
<212> TYPE: DNA
<213> ORGANISM: Artificial Sequence
<220> FEATURE:
<223> OTHER INFORMATION: primer TAAla-R

<400> SEQUENCE: 61
cgcctgagca atggcgacaa tgt                                              23

<210> SEQ ID NO 62
<211> LENGTH: 23
<212> TYPE: DNA
<213> ORGANISM: Artificial Sequence
<220> FEATURE:
<223> OTHER INFORMATION: primer TATyr-R

<400> SEQUENCE: 62
atactgagca atggcgacaa tgt                                              23

<210> SEQ ID NO 63
<211> LENGTH: 23
<212> TYPE: DNA
<213> ORGANISM: Artificial Sequence
<220> FEATURE:
<223> OTHER INFORMATION: primer TAHis-R

<400> SEQUENCE: 63
atgctgagca atggcgacaa tgt                                              23

<210> SEQ ID NO 64
<211> LENGTH: 23
<212> TYPE: DNA
<213> ORGANISM: Artificial Sequence
<220> FEATURE:
<223> OTHER INFORMATION: primer TAGln-R

<400> SEQUENCE: 64
ctgctgagca atggcgacaa tgt                                              23

<210> SEQ ID NO 65
<211> LENGTH: 23
<212> TYPE: DNA
<213> ORGANISM: Artificial Sequence
<220> FEATURE:
<223> OTHER INFORMATION: primer TAAsn-R

<400> SEQUENCE: 65
gttctgagca atggcgacaa tgt                                              23
```

<210> SEQ ID NO 66
<211> LENGTH: 23
<212> TYPE: DNA
<213> ORGANISM: Artificial Sequence
<220> FEATURE:
<223> OTHER INFORMATION: primer TALys-R

<400> SEQUENCE: 66
tttctgagca atggcgacaa tgt                                          23

<210> SEQ ID NO 67
<211> LENGTH: 23
<212> TYPE: DNA
<213> ORGANISM: Artificial Sequence
<220> FEATURE:
<223> OTHER INFORMATION: primer TAAsp-R

<400> SEQUENCE: 67
atcctgagca atggcgacaa tgt                                          23

<210> SEQ ID NO 68
<211> LENGTH: 23
<212> TYPE: DNA
<213> ORGANISM: Artificial Sequence
<220> FEATURE:
<223> OTHER INFORMATION: primer TAGlu-R

<400> SEQUENCE: 68
ttcctgagca atggcgacaa tgt                                          23

<210> SEQ ID NO 69
<211> LENGTH: 23
<212> TYPE: DNA
<213> ORGANISM: Artificial Sequence
<220> FEATURE:
<223> OTHER INFORMATION: primer TACys-R

<400> SEQUENCE: 69
gcactgagca atggcgacaa tgt                                          23

<210> SEQ ID NO 70
<211> LENGTH: 23
<212> TYPE: DNA
<213> ORGANISM: Artificial Sequence
<220> FEATURE:
<223> OTHER INFORMATION: primer TATrp-R

<400> SEQUENCE: 70
ccactgagca atggcgacaa tgt                                          23

<210> SEQ ID NO 71
<211> LENGTH: 23
<212> TYPE: DNA
<213> ORGANISM: Artificial Sequence
<220> FEATURE:
<223> OTHER INFORMATION: primer TAArg-R

<400> SEQUENCE: 71
tctctgagca atggcgacaa tgt                                          23

<210> SEQ ID NO 72
<211> LENGTH: 23
<212> TYPE: DNA
<213> ORGANISM: Artificial Sequence
<220> FEATURE:

```
<223> OTHER INFORMATION: primer TAGly-R

<400> SEQUENCE: 72
tccctgagca atggcgacaa tgt                                          23

<210> SEQ ID NO 73
<211> LENGTH: 20
<212> TYPE: DNA
<213> ORGANISM: Artificial Sequence
<220> FEATURE:
<223> OTHER INFORMATION: primer aspC1-F

<400> SEQUENCE: 73
ccagatcgat tctgacaaca                                              20

<210> SEQ ID NO 74
<211> LENGTH: 25
<212> TYPE: DNA
<213> ORGANISM: Artificial Sequence
<220> FEATURE:
<223> OTHER INFORMATION: primer aspC1-R

<400> SEQUENCE: 74
cccggagttt gtgccgtgcg agcac                                        25

<210> SEQ ID NO 75
<211> LENGTH: 25
<212> TYPE: DNA
<213> ORGANISM: Artificial Sequence
<220> FEATURE:
<223> OTHER INFORMATION: primer aspC2-F

<400> SEQUENCE: 75
gtgctcgcac ggcacaaact ccggg                                        25

<210> SEQ ID NO 76
<211> LENGTH: 36
<212> TYPE: DNA
<213> ORGANISM: Artificial Sequence
<220> FEATURE:
<223> OTHER INFORMATION: primer aspC2-R

<400> SEQUENCE: 76
cccaagcttg agtccgtgca aattcaaaat attgca                            36

<210> SEQ ID NO 77
<211> LENGTH: 22
<212> TYPE: DNA
<213> ORGANISM: Artificial Sequence
<220> FEATURE:
<223> OTHER INFORMATION: primer aspA-F

<400> SEQUENCE: 77
cagcatatga tctcgggtat tc                                           22

<210> SEQ ID NO 78
<211> LENGTH: 35
<212> TYPE: DNA
<213> ORGANISM: Artificial Sequence
<220> FEATURE:
<223> OTHER INFORMATION: primer aspA-R

<400> SEQUENCE: 78
cccaagcttg agtcctgctc acaagaaaaa aggca                             35
```

```
<210> SEQ ID NO 79
<211> LENGTH: 19
<212> TYPE: DNA
<213> ORGANISM: Artificial Sequence
<220> FEATURE:
<223> OTHER INFORMATION: primer ppc1-F

<400> SEQUENCE: 79
cgacctacac ctttggtgt                                                        19

<210> SEQ ID NO 80
<211> LENGTH: 34
<212> TYPE: DNA
<213> ORGANISM: Artificial Sequence
<220> FEATURE:
<223> OTHER INFORMATION: primer ppc1-R

<400> SEQUENCE: 80
cgcatctttt gctgaatcgg aatagccaat catc                                       34

<210> SEQ ID NO 81
<211> LENGTH: 34
<212> TYPE: DNA
<213> ORGANISM: Artificial Sequence
<220> FEATURE:
<223> OTHER INFORMATION: primer ppc2-F

<400> SEQUENCE: 81
gatgattggc tattccgatt cagcaaaaga tgcg                                       34

<210> SEQ ID NO 82
<211> LENGTH: 27
<212> TYPE: DNA
<213> ORGANISM: Artificial Sequence
<220> FEATURE:
<223> OTHER INFORMATION: primer ppc2-R

<400> SEQUENCE: 82
ggaatggcgc gtagtgattc gacgccg                                               27

<210> SEQ ID NO 83
<211> LENGTH: 27
<212> TYPE: DNA
<213> ORGANISM: Artificial Sequence
<220> FEATURE:
<223> OTHER INFORMATION: primer ppc3-F

<400> SEQUENCE: 83
cggcgtcgaa tcactacgcg ccattcc                                               27

<210> SEQ ID NO 84
<211> LENGTH: 34
<212> TYPE: DNA
<213> ORGANISM: Artificial Sequence
<220> FEATURE:
<223> OTHER INFORMATION: primer ppc3-R

<400> SEQUENCE: 84
tccgtagctg aatagattct gcaatccacg gcag                                       34

<210> SEQ ID NO 85
<211> LENGTH: 34
<212> TYPE: DNA
<213> ORGANISM: Artificial Sequence
<220> FEATURE:
<223> OTHER INFORMATION: primer ppc4-F
```

```
<400> SEQUENCE: 85
ctgccgtgga ttgcagaatc tattcagcta cgga                                    34

<210> SEQ ID NO 86
<211> LENGTH: 36
<212> TYPE: DNA
<213> ORGANISM: Artificial Sequence
<220> FEATURE:
<223> OTHER INFORMATION: primer ppc4-R

<400> SEQUENCE: 86
cccaagcttg agtcgaaaac gagggtgtta gaacag                                  36

<210> SEQ ID NO 87
<211> LENGTH: 22
<212> TYPE: DNA
<213> ORGANISM: Artificial Sequence
<220> FEATURE:
<223> OTHER INFORMATION: primer asd1-F

<400> SEQUENCE: 87
ctttctgcgt gctaacaaag ca                                                 22

<210> SEQ ID NO 88
<211> LENGTH: 33
<212> TYPE: DNA
<213> ORGANISM: Artificial Sequence
<220> FEATURE:
<223> OTHER INFORMATION: primer Asd1-R

<400> SEQUENCE: 88
catccgcttt cacggagctt tggatagatt tcg                                     33

<210> SEQ ID NO 89
<211> LENGTH: 33
<212> TYPE: DNA
<213> ORGANISM: Artificial Sequence
<220> FEATURE:
<223> OTHER INFORMATION: primer Asd2-F

<400> SEQUENCE: 89
cgaaatctat ccaaagctcc gtgaaagcgg atg                                     33

<210> SEQ ID NO 90
<211> LENGTH: 38
<212> TYPE: DNA
<213> ORGANISM: Artificial Sequence
<220> FEATURE:
<223> OTHER INFORMATION: primer Asd2-R

<400> SEQUENCE: 90
cccaagcttg agtcgctcta tttaactccc ggtaaatc                                38

<210> SEQ ID NO 91
<211> LENGTH: 19
<212> TYPE: DNA
<213> ORGANISM: Artificial Sequence
<220> FEATURE:
<223> OTHER INFORMATION: primer pntA/B1-F

<400> SEQUENCE: 91
ccactatcac ggctgaatc                                                     19

<210> SEQ ID NO 92
<211> LENGTH: 27
```

<212> TYPE: DNA
<213> ORGANISM: Artificial Sequence
<220> FEATURE:
<223> OTHER INFORMATION: primer pntA/B1-R

<400> SEQUENCE: 92
cggcacagaa tccatcgcca tcacggt                                            27

<210> SEQ ID NO 93
<211> LENGTH: 27
<212> TYPE: DNA
<213> ORGANISM: Artificial Sequence
<220> FEATURE:
<223> OTHER INFORMATION: primer pntA/B2-F

<400> SEQUENCE: 93
accgtgatgg cgatggattc tgtgccg                                            27

<210> SEQ ID NO 94
<211> LENGTH: 29
<212> TYPE: DNA
<213> ORGANISM: Artificial Sequence
<220> FEATURE:
<223> OTHER INFORMATION: primer pntA/B2-R

<400> SEQUENCE: 94
gccttcatgg aatcaaccat ttcacgggt                                          29

<210> SEQ ID NO 95
<211> LENGTH: 29
<212> TYPE: DNA
<213> ORGANISM: Artificial Sequence
<220> FEATURE:
<223> OTHER INFORMATION: primer pntA/B3-F

<400> SEQUENCE: 95
acccgtgaaa tggttgaatc catgaaggc                                          29

<210> SEQ ID NO 96
<211> LENGTH: 32
<212> TYPE: DNA
<213> ORGANISM: Artificial Sequence
<220> FEATURE:
<223> OTHER INFORMATION: primer pntA/B3-R

<400> SEQUENCE: 96
cagcatgcgc tgagtaacgg tgaagccacc ga                                      32

<210> SEQ ID NO 97
<211> LENGTH: 32
<212> TYPE: DNA
<213> ORGANISM: Artificial Sequence
<220> FEATURE:
<223> OTHER INFORMATION: primer pntA/B4-F

<400> SEQUENCE: 97
tcggtggctt caccgttact cagcgcatgc tg                                      32

<210> SEQ ID NO 98
<211> LENGTH: 31
<212> TYPE: DNA
<213> ORGANISM: Artificial Sequence
<220> FEATURE:
<223> OTHER INFORMATION: primer pntA/B4-R

<400> SEQUENCE: 98
accagcaatc ggactttcg gatcatcctg c                                      31

<210> SEQ ID NO 99
<211> LENGTH: 31
<212> TYPE: DNA
<213> ORGANISM: Artificial Sequence
<220> FEATURE:
<223> OTHER INFORMATION: primer pntA/B5-F

<400> SEQUENCE: 99
gcaggatgat ccgaaaagtc cgattgctgg t                                     31

<210> SEQ ID NO 100
<211> LENGTH: 33
<212> TYPE: DNA
<213> ORGANISM: Artificial Sequence
<220> FEATURE:
<223> OTHER INFORMATION: primer pntA/B5-R

<400> SEQUENCE: 100
cccaagcttg agtctgggta tgctgctttc cgt                                   33

<210> SEQ ID NO 101
<211> LENGTH: 37
<212> TYPE: DNA
<213> ORGANISM: Artificial Sequence
<220> FEATURE:
<223> OTHER INFORMATION: primer rhtA-F

<400> SEQUENCE: 101
cccaagcttg agtcaaagga tgcctggttc attacgt                               37

<210> SEQ ID NO 102
<211> LENGTH: 22
<212> TYPE: DNA
<213> ORGANISM: Artificial Sequence
<220> FEATURE:
<223> OTHER INFORMATION: primer rhtA-R

<400> SEQUENCE: 102
ctaatagtgg taacaagcgt ga                                               22

<210> SEQ ID NO 103
<211> LENGTH: 38
<212> TYPE: DNA
<213> ORGANISM: Artificial Sequence
<220> FEATURE:
<223> OTHER INFORMATION: primer rhtB-F

<400> SEQUENCE: 103
cccaagcttg agtctcatca tgaccttaga atggtggt                              38

<210> SEQ ID NO 104
<211> LENGTH: 18
<212> TYPE: DNA
<213> ORGANISM: Artificial Sequence
<220> FEATURE:
<223> OTHER INFORMATION: primer rhtB-R

<400> SEQUENCE: 104
gcgtggttta ccgtcgtt                                                    18

<210> SEQ ID NO 105
<211> LENGTH: 42
<212> TYPE: DNA
<213> ORGANISM: Artificial Sequence
<220> FEATURE:
<223> OTHER INFORMATION: primer rhtC-F

<400> SEQUENCE: 105
cccaagcttg agtcaatgta tgttgatgtt atttctcacc gt					42

<210> SEQ ID NO 106
<211> LENGTH: 20
<212> TYPE: DNA
<213> ORGANISM: Artificial Sequence
<220> FEATURE:
<223> OTHER INFORMATION: primer rhtC-R

<400> SEQUENCE: 106
cttgctcaac ggattgctct					20

<210> SEQ ID NO 107
<211> LENGTH: 36
<212> TYPE: DNA
<213> ORGANISM: Artificial Sequence
<220> FEATURE:
<223> OTHER INFORMATION: primer yecC-F

<400> SEQUENCE: 107
cccaagcttg agtcccaaaa tgagtgccat tgaagt					36

<210> SEQ ID NO 108
<211> LENGTH: 24
<212> TYPE: DNA
<213> ORGANISM: Artificial Sequence
<220> FEATURE:
<223> OTHER INFORMATION: primer yecC-R

<400> SEQUENCE: 108
agttatgctg atttgttaag cagt					24

<210> SEQ ID NO 109
<211> LENGTH: 39
<212> TYPE: DNA
<213> ORGANISM: Artificial Sequence
<220> FEATURE:
<223> OTHER INFORMATION: primer T-F

<400> SEQUENCE: 109
cccaagcttg agtcccaaac aattccgacg tctaagaag					39

<210> SEQ ID NO 110
<211> LENGTH: 44
<212> TYPE: DNA
<213> ORGANISM: Artificial Sequence
<220> FEATURE:
<223> OTHER INFORMATION: primer TBCD-R

<400> SEQUENCE: 110 ctcctttta agtgaacttg ggcccggtca gtgcgtcctg ctga					44

<210> SEQ ID NO 111
<211> LENGTH: 44
<212> TYPE: DNA
<213> ORGANISM: Artificial Sequence
<220> FEATURE:
<223> OTHER INFORMATION: primer TBCD-F

<400> SEQUENCE: 111
tcagcaggac gcactgaccg ggcccaagtt cacttaaaaa ggag					44

<210> SEQ ID NO 112
<211> LENGTH: 21
<212> TYPE: DNA
<213> ORGANISM: Artificial Sequence
<220> FEATURE:
<223> OTHER INFORMATION: primer BCD-R

<400> SEQUENCE: 112
tagaaagtct cctgtgcatg a                                              21

<210> SEQ ID NO 113
<211> LENGTH: 40
<212> TYPE: DNA
<213> ORGANISM: Artificial Sequence
<220> FEATURE:
<223> OTHER INFORMATION: primer TGB-F

<400> SEQUENCE: 113
agggagaaag gcggacaggt tccggtaag cggcagggtc                          40

<210> SEQ ID NO 114
<211> LENGTH: 40
<212> TYPE: DNA
<213> ORGANISM: Artificial Sequence
<220> FEATURE:
<223> OTHER INFORMATION: primer TGB-R

<400> SEQUENCE: 114
gaccctgccg cttaccggaa acctgtccgc ctttctccct                         40

<210> SEQ ID NO 115
<211> LENGTH: 59
<212> TYPE: DNA
<213> ORGANISM: Artificial Sequence
<220> FEATURE:
<223> OTHER INFORMATION: primer N20-ilvA-F

<400> SEQUENCE: 115
tcctaggtat aatactagtc ttcatcaaag ttcgcgccgg ttttagagct agaaatagc    59

<210> SEQ ID NO 116
<211> LENGTH: 59
<212> TYPE: DNA
<213> ORGANISM: Artificial Sequence
<220> FEATURE:
<223> OTHER INFORMATION: primer N20-ilvA-R

<400> SEQUENCE: 116
gctatttcta gctctaaaac cggcgcgaac tttgatgaag actagtatta tacctagga   59

<210> SEQ ID NO 117
<211> LENGTH: 59
<212> TYPE: DNA
<213> ORGANISM: Artificial Sequence
<220> FEATURE:
<223> OTHER INFORMATION: primer N20-tdh-R

<400> SEQUENCE: 117
tcctaggtat aatactagtc tttggcgacg ttaaccgcag ttttagagct agaaatagc   59

<210> SEQ ID NO 118
<211> LENGTH: 59
<212> TYPE: DNA
<213> ORGANISM: Artificial Sequence
<220> FEATURE:
<223> OTHER INFORMATION: primer N20-tdh-R

<400> SEQUENCE: 118
gctatttcta gctctaaaac tgcggttaac gtcgccaaag actagtatta tacctagga    59

<210> SEQ ID NO 119
<211> LENGTH: 40
<212> TYPE: DNA
<213> ORGANISM: Artificial Sequence
<220> FEATURE:
<223> OTHER INFORMATION: primer ilv1-F

<400> SEQUENCE: 119
ctacgaaggt gcattgaagg ggatgcagga aatgctctac    40

<210> SEQ ID NO 120
<211> LENGTH: 41
<212> TYPE: DNA
<213> ORGANISM: Artificial Sequence
<220> FEATURE:
<223> OTHER INFORMATION: primer ilv1-R

<400> SEQUENCE: 120
gcgctatcag gcattttcc tattaacccc ccagtttcga t    41

<210> SEQ ID NO 121
<211> LENGTH: 41
<212> TYPE: DNA
<213> ORGANISM: Artificial Sequence
<220> FEATURE:
<223> OTHER INFORMATION: primer ilv2-F

<400> SEQUENCE: 121
atcgaaactg gggggttaat aggaaaaatg cctgatagcg c    41

<210> SEQ ID NO 122
<211> LENGTH: 40
<212> TYPE: DNA
<213> ORGANISM: Artificial Sequence
<220> FEATURE:
<223> OTHER INFORMATION: primer ilv2-R

<400> SEQUENCE: 122
agttggagaa caggtacgga cgtaatcagg tgtcggtaga    40

<210> SEQ ID NO 123
<211> LENGTH: 40
<212> TYPE: DNA
<213> ORGANISM: Artificial Sequence
<220> FEATURE:
<223> OTHER INFORMATION: primer tdh1-F

<400> SEQUENCE: 123
tctaccgaca cctgattacg tccgtacctg ttctccaact    40

<210> SEQ ID NO 124
<211> LENGTH: 40
<212> TYPE: DNA
<213> ORGANISM: Artificial Sequence
<220> FEATURE:
<223> OTHER INFORMATION: primer tdh1-R

<400> SEQUENCE: 124
gaataccagc ccttgttcgt ctcacatcct caggcgataa    40

<210> SEQ ID NO 125

```
<211> LENGTH: 40
<212> TYPE: DNA
<213> ORGANISM: Artificial Sequence
<220> FEATURE:
<223> OTHER INFORMATION: primer tdh2-F

<400> SEQUENCE: 125
ttatcgcctg aggatgtgag acgaacaagg gctggtattc                              40

<210> SEQ ID NO 126
<211> LENGTH: 33
<212> TYPE: DNA
<213> ORGANISM: Artificial Sequence
<220> FEATURE:
<223> OTHER INFORMATION: primer tdh2-R

<400> SEQUENCE: 126
cgcggatccc agaattatcc gttgaaccat cgt                                     33

<210> SEQ ID NO 127
<211> LENGTH: 40
<212> TYPE: DNA
<213> ORGANISM: Artificial Sequence
<220> FEATURE:
<223> OTHER INFORMATION: primer sgRNA-F

<400> SEQUENCE: 127
cccaagcttg tatcccgctt accttgacag ctagctcagt                              40

<210> SEQ ID NO 128
<211> LENGTH: 19
<212> TYPE: DNA
<213> ORGANISM: Artificial Sequence
<220> FEATURE:
<223> OTHER INFORMATION: primer sgRNA-R

<400> SEQUENCE: 128
tgcaggtcga ctctagaga                                                     19

<210> SEQ ID NO 129
<211> LENGTH: 21
<212> TYPE: DNA
<213> ORGANISM: Artificial Sequence
<220> FEATURE:
<223> OTHER INFORMATION: primer TG-F

<400> SEQUENCE: 129
gaactcgagt agggataaca g                                                  21

<210> SEQ ID NO 130
<211> LENGTH: 22
<212> TYPE: DNA
<213> ORGANISM: Artificial Sequence
<220> FEATURE:
<223> OTHER INFORMATION: primer ilvA-I-F

<400> SEQUENCE: 130
acgatgcggt agaagcgatt ct                                                 22

<210> SEQ ID NO 131
<211> LENGTH: 23
<212> TYPE: DNA
<213> ORGANISM: Artificial Sequence
<220> FEATURE:
<223> OTHER INFORMATION: primer ilvA-I-R

<400> SEQUENCE: 131
```

```
gagaatctgg cagtagtgct gat                                              23

<210> SEQ ID NO 132
<211> LENGTH: 23
<212> TYPE: DNA
<213> ORGANISM: Artificial Sequence
<220> FEATURE:
<223> OTHER INFORMATION: primer tdh-I-F

<400> SEQUENCE: 132
atattatcac cggtacgctt ggt                                              23

<210> SEQ ID NO 133
<211> LENGTH: 22
<212> TYPE: DNA
<213> ORGANISM: Artificial Sequence
<220> FEATURE:
<223> OTHER INFORMATION: primer tdh-I-R

<400> SEQUENCE: 133
gcctgatgca acaaacgaac gt                                               22

<210> SEQ ID NO 134
<211> LENGTH: 16
<212> TYPE: DNA
<213> ORGANISM: Artificial Sequence
<220> FEATURE:
<223> OTHER INFORMATION: position signals of mCherry gene

<400> SEQUENCE: 134
tactcgactc gcatgc                                                      16
```

DNA ASSEMBLY METHOD AND ITS APPLICATION

CROSS-REFERENCE TO RELATED APPLICATIONS

This application claims priority under 35 U.S.C. § 119(b) to Chinese Application No. 201811613376.4, filed Dec. 27, 2018, the disclosure of which is incorporated herein by reference in its entirety.

REFERENCE TO SEQUENCE LISTING SUBMITTED ELECTRONICALLY

This application contains a sequence listing, which is submitted electronically via EFS-Web as an ASCII formatted sequence listing with a file name "Updated Sequence Listing 689413.0011", creation date of Jul. 26, 2021, and having a size of about 64 KB. The sequence listing submitted via EFS-Web is part of the specification and is herein incorporated by reference in its entirety.

TECHNICAL FIELD

The present invention relates generally to the biotechnological field, and in particular to a DNA assembly method and its application.

BACKGROUND

DNA assembly is the basic enabling technology for synthetic biology and bioengineering. Currently, DNA assembly methods fall into two main categories: assembly strategies based on Restriction endonucleases (RE) and assembly strategies based on homologous fragments. The RE-based DNA assembly methods are the most widely used assembly methods.

In the development of RE-based DNA assembly methods, the BioBrick™ method (Shetty, R P, Endy, D., and Knight, T. F, Jr. (2008) Engineering BioBrick vectors from BioBrick parts, J Biol Eng 2, 5) is the first method that was developed and put into practical use. This method utilizes four Type IIP REs (e.g., EcoRI, XbaI, SpeI, and PstI) for the recyclable DNA fragment assembly, in which two Type IIP REs (e.g., XbaI and SpeI) are isocaudomers.

By adding the EcoRI/XbaI site and the SpeI/PstI site at the 5' end of a DNA fragment, the BioBrick™ method ensures that the recombinant vector still remains singular EcoRI/XbaI site and the SpeI/PstI site to achieve recyclability of the enzymes and the vector, thereby integrating new fragments into the assembled DNA in a continuously cyclic (recursive) way. This recursive DNA assembly method can achieve multiple rounds of "design-build-test" cycle to solve bioengineering trial and error verification studies without adequate mastery of genetic, physiological, and metabolic mechanisms. Especially in metabolic engineering studies, multiple rounds of "design-build-test" cycle can gradually solve the problems such as key enzyme screening, metabolic bottleneck removal, metabolic flux optimization and metabolic pathway reconstruction, gradually increase the yield, transformation rate and production intensity of specific metabolites, and build high-performance engineered strain to meet the needs of industrial production.

The easy-to-use and recursive assembly of the BioBrick™ method has led to its widespread use, and a number of similar DNA assembly methods have been derived therefrom, such as BglBrick (Anderson, J. C., Dueber, J. E., Leguia, M., Wu, G. C., Goler, J. A., Arkin, A. P., and Keasling, J. D. (2010) BglBricks: A flexible standard for biological part assembly, J Biol Eng 4, 1), iBrick (Liu, J. K., Chen, W. H., Ren, S. X., Zhao, G. P., and Wang, J. (2014) iBrick: A New Standard for Iterative Assembly of Biological Parts with Homing Endonucleases, Plos One 9), C-Brick (Li, S. Y., Zhao, G. P., and Wang, J. (2016) C-Brick: A New Standard for Assembly of Biological Parts Using Cpf1, Acs Synth Biol 5, 1383-1388), and YaliBrick (Wong, L., Engel, J., Jin, E., Holdridge, B., and Xu, P. (2017) YaliBricks, a versatile genetic toolkit for streamlined and rapid pathway engineering in *Yarrowia lipolytica*, Metab Eng Commun 5, 68-77). However, these methods introduce extra base sequences ("SCAR sequences") at the position where a pair of isocaudomers of the DNA fragment are fused. For example, the BioBrick™ method produces 8 bp SCAR sequences, and the BglBrick, C-Brick, CCTL, and YaliBrick methods will produce 6 bp SCAR sequences. The SCAR sequence between the spliced DNA fragments affects the integrity of the DNA sequence, the secondary structure of the mRNA, and the correct expression of the protein, increasing the difficulty of DNA sequence design and limiting its application in the need for SCAR-free assembly and precise assembly. In particular, genetic elements that affect the function of upstream and downstream sequences, such as enhancers, promoters, RBS, spacer sequences, coding sequences, and terminator sequences, are accurately assembled into open reading frames, gene loops, metabolic pathways, or metabolic modules. It is desired to solve the problem of SCAR sequences in BioBrick™ and its derived assembly methods and develop a SCAR-free recursive DNA assembly technique.

SUMMARY

The present invention establishes a SCAR-free PS-Brick assembly method for the "SCAR" sequence problem in the above-described recursive DNA assembly method. The method simultaneously uses the Type IIP and Type IIS REs, and combines the characteristics of the PCR product to realize the SCAR-free, iterative and tandem repeat sequence assembly, and has the characteristics of cost effectiveness and ease of use. This method is used for metabolic engineering of threonine strains, including thrA site mutation screening and modular integration with thrB, thrC, elimination of metabolic bottlenecks, identification of core efflux genes, and assembly of CRISPR-sgRNA repeat alignment vectors for co-knockout of threonine catabolic pathway-related genes. Moreover, through several rounds of "design-build-test" cycle, the method builds an engineering strain with high accumulation of threonine, which proves the industrial applicability of the method.

The present invention provides a plasmid comprising single adjacent Type IIP and Type IIS RE recognition sites.

Preferably, according to the above-described plasmid, the Type IIP RE is a Type IIP RE which cleaves to produce sticky ends with two or more bases.

Preferably, according to the above-described plasmid, the Type IIS RE is a Type IIS RE which cleaves to produce single-base sticky ends; or a Type IIS RE which cleaves to produce blunt ends.

More preferably, according to the above-described plasmid, the Type IIS RE is BmrI, BciVI, HphI or MlyI.

The present invention further provides a DNA assembly method, comprising: (1) performing a single-ended ligation of a gene to be inserted (i.e., a template) into a DNA fragment containing adjacent Type IIP and Type IIS RE recognition sites to obtain a target gene; (2) cleaving the target gene using the corresponding Type IIP RE to obtain a donor DNA; (3) cleaving the above plasmid using the corresponding Type IIP and Type IIS REs to obtain an acceptor DNA, wherein the plasmid comprises the same Type IIP and Type IIS RE recognition sites as the target gene; and (4) ligating the donor DNA to the acceptor DNA.

Preferably, according to the above method, in the target gene, the Type IIP RE recognition site is outside the Type IIS RE recognition site.

Preferably, according to the above method, when the Type IIS RE is a Type IIS RE which cleaves to produce single-base sticky ends, the step (1) further comprises attaching an A base to the other end of the gene to be inserted.

Preferably, according to the above method, in step (3), the plasmid is first cleaved using a corresponding Type IIP RE to obtain a linearized plasmid, and the linearized plasmid is cleaved using a corresponding Type IIS RE.

The present invention further provides a recombinant strain constructed according to the above method.

Preferably, according to the above recombinant strain, the recombinant strain is a recombinant strain producing threonine, and has increased expression of aspartate kinase ThrA, homoserine kinase ThrB, threonine synthase ThrC, aspartate semialdehyde dehydrogenase Asd, and threonine efflux transporter RhtC as compared with the original strain and has reduced expression of threonine dehydrogenase Tdh and threonine dehydratase IlvA as compared with the original strain.

More preferably, the increase in expression is achieved by transforming a plasmid carrying the corresponding gene to the original strain, and the reduction in expression is achieved by knocking out the corresponding gene of the original strain.

Further preferably, the plasmid carrying the corresponding gene is constructed by the above method, and a vector for knocking out the corresponding gene is constructed by the above method.

The present application discloses a DNA assembly method based on Type IIP and Type IIS REs, i.e., PS-Brick. The method combines the properties of PCR products, Type IIP and Type IIS REs to achieve recursive cycling, SCAR-free and repeat sequence assembly. The PS-Brick assembly method is used for metabolic engineering breeding, which has industrial applicability: based on the advantage of seamless assembly of this method, the codon saturation mutagenesis and the precise splicing of the bicistronics are realized; based on the advantage of the tandem repeat fragment assembly of this method, the tandem CRISSPR sgRNA repeats with the same promoter and terminator are assembled; based on the cyclic iterative assembly characteristics of PS-Brick, the feedback inhibition of threonine biosynthesis is gradually eliminated, the metabolic bottleneck is eliminated, threonine efflux is strengthened, the threonine catabolism is inactivated, and the metabolic pathway of threonine is systematically optimized and transformed, and an engineering strain for efficient production of threonine is obtained. In addition, the PS-Brick assembly method has the advantages of simplicity, time saving and high efficiency, and has high practicability.

Compared with the existing DNA assembly technique, the novel design of the PS-Brick assembly method is mainly reflected in the following aspects:

(1) Existing RE-based DNA assembly methods (such as the BioBrick and Golden Gate assembly methods) use only one type of RE, i.e., Type IIP or Type IIS REs, respectively. The method of the present invention uses REs of both Type IIP and Type IIS, to achieve both recursive and non-marking advantages of the above two methods.

(2) The target gene hangs the adjacent RE recognition sites only at a single end, so that a blunt end or an A-binding sticky end at the other end of the target gene can be simultaneously utilized.

(3) A Type IIS RE producing blunt ends and a blunt-ended target gene, or a Type IIS RE producing single-base sticky ends and a target gene with A-binding sticky ends are used to achieve SCAR-free splicing of DNA fragments.

(4) A single pair of adjacent Type IIP and Type IIS RE sites form recyclable import sites for recursive cycling assembly.

The recognition and restriction sites of the Type IIP RE are of the same palindromic sequence. At present, Type IIP RE-based DNA assembly methods can only use four specific REs at the same time. For example, the BioBrick method can only use SpeI, PstI, XbaI and SpeI at the same time; BglBrick can only use EcoRI, BglII, BamHI, and XhoI at the same time; YaliBrick can only use SpeI, XbaI, NheI, and AvrII at the same time. The PS-Brick assembly technique can use any of the hundreds of Type IIP REs that produce sticky ends with two or more bases, greatly reducing site restriction and increasing the sequence design of the PS-Brick assembly method.

The restriction site of the Type IIS RE is outside the recognition site, and different Type IIS REs can produce sticky ends with 1-4 bases, respectively, and can also produce blunt ends. PS-Brick only uses Type IIS REs that produce blunt ends or single-base sticky ends. Currently, three single-base sticky end Type IIS REs (BmrI, BciVI and HphI) and a blunt-ended Type IIS RE MlyI can be purchased through commercial channels.

In addition, primers for PCR amplification of donor DNA do not require special modifications (e.g., 5'port phosphorylation), thereby reducing the application cost of the present technique.

DETAILED DESCRIPTION OF EMBODIMENTS

Figure 1:
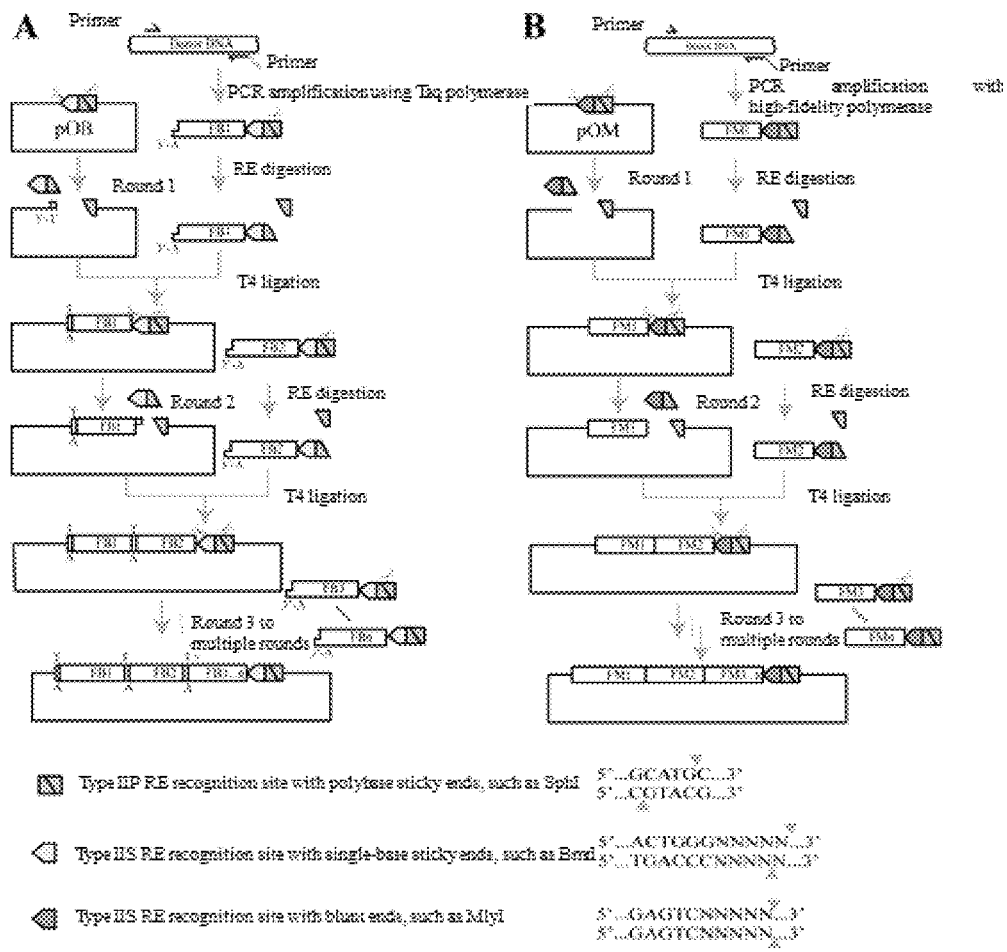
FIG. 1 is a design principle and operation flowchart of the PS-Brick assembly method.

The embodiments of the present invention will be described in more detail in conjunction with the accompanying drawings and embodiments, in order to provide a better understanding of the embodiments of the present invention and the advantages thereof. However, the specific embodiments and examples described below are illustrative only and should be construed as limiting the present invention.

The present invention cites publications for the purpose of more clearly describing the present invention. These publications are hereby incorporated by reference in their entireties as if their full texts have been repeatedly described herein.

The order of execution of the steps in the method mentioned in the present invention is not limited to the order shown in the text of the present invention unless otherwise specified, that is, the order of execution of the steps may be changed, and between two steps, additional steps may be inserted as needed.

The "original strain" referred to in the present invention means the initial strain used in the genetic modification strategy of the present invention. The strain may be a naturally occurring strain, or may be a strain bred by mutagenesis or genetic engineering. In order to build an engineered strain for producing threonine, the original bacterium is preferably a strain capable of accumulating threonine.

The expression "increased expression of . . . " as used in the present invention is intended to indicate that the expression of a protein encoded by the corresponding gene is increased. It can be achieved by overexpression of the corresponding gene, for example, by constructing a recombinant plasmid containing the gene, and then introducing the recombinant plasmid in the original strain; it can also be achieved by inserting the gene into the chromosome in the original strain. These methods are commonly used in the art and will not be described again. The vector used to construct the recombinant plasmid is not limited and may be any suitable plasmid, for example, pXMJ19.

The expression "reduced expression of . . . " as used in the present invention is intended to indicate that the expression of a protein encoded by the corresponding gene is reduced. It can be achieved by inactivating the corresponding gene, and "inactivating" refers to a change in the corresponding engineered object, thereby achieving certain effects, including but not limited to, site-directed mutagenesis, insertional inactivation, and/or knockout.

The "ligation . . . recognition sites" referred to in the present invention can be introduced by PCR primers.

The target gene may be a PCR product having a prominent single "A" base at the 3' end amplified by a DNA polymerase such as Taq, LA Taq or EX Taq, or a blunt-ended PCR product amplified by high-fidelity polymerases such as Q5, KAPA, KOD or Pfu.

The experimental methods in the following examples are conventional methods unless otherwise specified. The test materials used in the following examples, unless otherwise specified, are purchased from conventional biochemical reagent stores. For the quantitative tests in the following examples, three replicate experiments are set, and the results are averaged. Unless otherwise specified in the following examples, the technical means used in the examples are conventional means well known to those skilled in the art and commercially available instruments and reagents, see "Molecular Cloning: A Laboratory Manual (3rd Edition)" (Science Press), "Microbiology Experiment (4th Edition)" (Higher Education Press), the manufacturer's instructions for the corresponding instruments and reagents, etc.

RE BciVI is purchased from Thermo Fisher Scientific, and other REs are purchased from New England Biolabs (NEB). Kapa hot start high-fidelity polymerase is purchased from Kapa Biosystems, Inc., and Ex-Taq DNA polymerase is purchased from TaKaRa-Bio.

The strains, plasmids and primer sequences (5' →3') used in the examples are as follows:

| Strain and plasmid Strain | Related characteristics | Source |
|---|---|---|
| E. coli DH5α | F− endA1 gln V44 thi-1 recA1 relA1 gyrA96 deoR nupG ϕ80dlacZΔM15 Δ(lacZYA-argF)U169 hsdR17 $(r_K^- m_K^+)\lambda^-$ | Invitrogen |
| E. coli MG1655 | K-12; F− λ− rph-1 | ATCC #700926 |
| MG1655Δ2 | MG1655ΔilvAΔtdh | The present patent |
| Plasmid | | |
| pUC19 | Vector backbone, pMB1 ori Ampr | TaKaRa #D3219 |
| pO19 | pUC19 with three mutated BciVI sites and one mutated BmrI site | The present patent |
| pOB | pO19 carrying truncated mCherry gene segment with SphI/BmrI entrance site | The present patent |
| pOM | pUC19 carrying truncated mCherry gene segment with SphI/MlyI entrance site | The present patent |
| pACYC184 | Vector backbone, p15A ori Cmr | New England Biolabs |

-continued

| Strain and plasmid Strain | Related characteristics | Source |
|---|---|---|
| pO184 | pACYC184 718T/A, 1150A/T, 3219A/T | The present patent |
| pOthr | pO184 carrying truncated thrABC genes with adjacent HindIII/MlyI entrance site | The present patent |
| pthrA433BC series | pOthr carrying partial thrA* encoding gene with 20 different codon saturation mutagenesis (Phe:TTT, Leu:CTG, Ile:ATT, Met:ATG, Val:GTG, Ser:AGC, Pro:CCG, Thr:ACC, Ala:GCG, Tyr:TAT, His:CAT, Gln:CAG, Asn:AAC, Lys:AAA, Asp:GAT, Glu:GAA, Cys:TGC, Trp:TGG, Arg:AGA, Gly:CGT) in the 433th residue | The present patent |
| pthrA433pheBC-aspA | pthrA433pheBC carrying aspA gene | The present patent |
| pthrA433pheBC-aspC | pthrA433pheBC carrying aspC gene | The present patent |
| pthrA433pheBC-ppc | pthrA433pheBC carrying ppc gene | The present patent |
| pthrA433pheBC-asd | pthrA433pheBC carrying asd gene | The present patent |
| pthrA433pheBC-pntA/B | pthrA433pheBC carrying pntAB gene | The present patent |
| pthrA433pheBC-asd-rhtA | pthrA433pheBC-asd carrying rhtA coding sequence with PT promoter and BCD1 | The present patent |
| pthrA433pheBC-asd-rhtB | pthrA433pheBC-asd carrying rhtB coding sequence with PT promoter and BCD1 | The present patent |
| pthrA433pheBC-asd-rhtC | pthrA433pheBC-asd carrying rhtC coding sequence with PT promoter and BCD1 | The present patent |
| pthrA433pheBC-asd-yecC | pthrA433pheBC-asd carrying yecC coding sequence with PT promoter and BCD1 | The present patent |
| pCas | repA101(Ts) kan Pcas-cas9 ParaB-Red lacIq Ptrc-sgRNA-Pmb1 | Jiang, Y., Chen, B., Duan, C. L., Sun, B. B., Yang, J. J., and Yang, S. (2015) |
| pTargetF | vector backbone for expressing sgRNA, Pmb1ori Ampr, | Multigene Editing in the *Escherichia coli* Genome via the CRISPR-Cas9 System, Appl Environ Microb 81, 2506-2514. |
| pTargetF-tdh | pTargetF carrying sgRNA with an N20 sequence for targeting the tdh locus, N20+PAM: CCGTGCGGTTAACGTCGCCAAA | The present patent |
| pTargetF-ilvA | pTargetF carrying sgRNA with an N20 sequence for targeting the ilvA locus, N20+PAM: CTTCATCAAAGTTCGCGCCGTGG | The present patent |
| pTargetET | pEC891 carrying editing templates of ilvA(805 bp) and tdh(785 bp), initial acceptor receptor for CRISPR array assembly | The present patent |

-continued

| Strain and plasmid Strain | Related characteristics | Source |
|---|---|---|
| ptargetET-tdh | pTargetET carrying sgRNA-tdh fragment | The present patent |
| ptargetET-tdh-ilvA | pTargetET carrying sgRNA-tdh fragment and sgRNA-ilvA fragment | The present patent |

| Name of primer | Sequence (5'-3') | Remarks |
|---|---|---|
| For PS-Brick assembly | | |
| UC709-F | TGCGTATTGGGCGCTCTTCCGCTTCCTCGC TCACTGACACGCTGCGCTCGGTCGTTCG | MlyI$^{T709A}$ mutation |
| UC1179-R | GTCGTGTCTTACCGGGTTGGAATCAAGACG ATAGTTACCGGAT | MlyI$^{G1179T}$ mutation |
| UC1179-F | ATCCGGTAACTATCGTCTTGATTCCAACCCG GTAAGACACGAC | |
| UC1695-R | TGGTAAGCCCTCCCGTATCGTAGTTATCTACA CGACGGGAGCCAGGCAA CTATGGATG | MlyI$^{A1695G}$ mutation |
| UC1746-R | AGCGTGGGTCTCGCGGTATC ATTGCAGCACT AGGGCCAGA TGGTAAGCCC TCCCGTATC | BmrI$^{C1746T}$ mutation |
| pUC19-MlyI$^{1177}$-R | GTCGTGTCTTACCGGGTTGG AATCAAGACGA TAGTTACCG GAT | |
| UC1 | GCACAGATGCGTAAGGAGA | For identifying |
| UC2 | GCAGGAAAGAACATGTGAGCA | plasmid pO19 |
| UC3 | AGGATCTTCACCTAGATCCT | |
| UC4 | GTTCGATGTAACCCACTCGT | |
| mC-F | GGGAATTCCATATGATGGTGAGCAAGGGCG AGGA(NdeI) | For amplifying the truncated mCherry |
| mCB-R | ACATGCATGCACTGGGGAGGAGTCCTGGGT CACGGTCA(SphI/BmrI) | gene fragment |
| mCM-R | ACATGCATGCGAGTCGAGTAGTCCTGGGTC ACGGTCA | (SphI/MlyI) |
| FB-F | CCTCCCTGCAGGACGGCGAGT | |
| FB-R | ACATGCATGCACTGGGTACTTGTACAGCT CGTCCA | For amplifying FB (SphI/BmrI) |
| FM-F | TCCTCCCTGCAGGACGGCGAGT | For amplifying FM |
| FM-R | ACATGCATGCGAGTCTACTTGTACAGCTC GTCCA(SphI/MlyI) | |
| UC 5 | ACGGTGAAAACC TCTGACACA | For identifying |
| UC6 | CGCAACGCAATTAATGTGAGT | plasmids pOB and pOM |
| For threonine pathway engineering | | |
| AC$^{3211}$-F | ACCACGATACTATGACTGAGTGTCAACGCC ATGAGCGGCC TCA | For mutating three MlyI sites of the |
| AC$^{727}$-R | GAACGACCGAGCGTAGCGTG TCAGTGAG CG AGGAAG | pACYC184 vector |
| AC$^{727}$-F | CTTCCTCGCTCACTGACACGC TACGCTCG GT CGTTC | |
| AC1143-R | AGTGGTGCTTTTGCATGTCTTTCCGGGTTG GAATCAAGAC GATAGTTACC GGATAAGGC | |
| TAB-F | CCCAAGCTTGAGTCAGGGATCTTCTGAACG CTCAATCTCT(HindIII/MlyI) | For overlap PCR to fuse thrB, thrC and |
| TAB-R | GGCATAAACTTTAACCATGTCAAACTCCTAA CTTCCATGAGAGGGTACG | truncated thrA. Gray indicates MlyI and |
| TBC-F | CGTACCCTCTCATGGAAGTTAGGAGTTTGAC ATGGTTAAAGTTTATGCC | HindIII site mutations. |
| TBC-R | GCTCACGTCCATCGCGTTGGATAACGTCGCCT GCGTCGCTTTGGGTGACCACTG | |
| TC-F | GCAGGCGACGTT ATCCAACGCGATGGACGTG A GCCAGCCGAA CAACTGGC | |
| TC-R | CCCTCGCGAGCATTATTGAGAATTTCTCC(NruI) | |
| TA-F | CCCAAGCTTGAGTCCTGGT CGACTGGTTA CAACA(HindIII/MlyI) | For the saturation mutagenesis of the |
| TA$^{phe}$-R | AAACTGAGCAATGGCGACAATGT | 433th residue of |
| TA$^{Leu}$-R | CAGCTGAGCAATGGCGACAATGT | ThrA. |
| TA$^{Ile}$-R | AATCTGAGCAATGGCGACAATGT | |

-continued

| Name of primer | Sequence (5'-3') | Remarks |
|---|---|---|
| TA<sup>Met</sup>-R | CATCTGAGCAATGGCGACAATGT | |
| TA<sup>Val</sup>-R | CACCTGAGCAATGGCGACAATGT | |
| TA<sup>Ser</sup>-R | GCTCTGAGCAATGGCGACAATGT | |
| TA<sup>Pro</sup>-R | CGGCTGAGCAATGGCGACAATGT | |
| TA<sup>Thr</sup>-R | GGTCTGAGCAATGGCGACAATGT | |
| TA<sup>Ala</sup>-R | CGCCTGAGCAATGGCGACAATGT | |
| TA<sup>Tyr</sup>-R | ATACTGAGCAATGGCGACAATGT | |
| TA<sup>His</sup>-R | ATGCTGAGCAATGGCGACAATGT | |
| TA<sup>Gln</sup>-R | CTGCTGAGCAATGGCGACAATGT | |
| TA<sup>Asn</sup>-R | GTTCTGAGCAATGGCGACAATGT | |
| TA<sup>Lys</sup>-R | TTTCTGAGCAATGGCGACAATGT | |
| TA<sup>Asp</sup>-R | ATCCTGAGCAATGGCGACAATGT | |
| TA<sup>Glu</sup>-R | TTCCTGAGCAATGGCGACAATGT | |
| TA<sup>Cys</sup>-R | GCACTGAGCAATGGCGACAATGT | |
| TA<sup>Trp</sup>-R | CCACTGAGCAATGGCGACAATGT | |
| TA<sup>Arg</sup>-R | TCTCTGAGCAATGGCGACAATGT | |
| TA<sup>Gly</sup>-R | TCCCTGAGCAATGGCGACAATGT | |
| aspC1-F | CCAGATCGAT TCTGACAACA | For mutating the MlyI site of aspC CCGGG gene |
| aspC1-R | CCCGGAGTTTGTGCCGTGCG AGCAC | |
| aspC2-F | GTGCTCGCACGGCACAAACT CCGGG | |
| aspC2-R | CCCAAGCTTGAGTCGTGCAAATTCAAAAT ATTGCA(HindIII/MlyI) | |
| aspA-F | CAGCATATGATC TCGGGTATTC | For amplifying aspA gene |
| aspA-R | CCCAAGCTTGAGTC CTGCTCACAA GAAA AAAGGCA(HindIII/MlyI) | |
| ppc1-F | CGACCTACACCTTTGG TGT | For mutating the site of ppc gene |
| ppc1-R | CGCATCTTTTGCTGAATCGG AATAGCCAAT CATC | |
| ppc2-F | GATGATTGGCTATTCCGATT CAGCAAAAGA TGCG | |
| ppc2-R | GCAATGGCGCGTAGTGATTC GACGCCG | |
| ppc3-F | CGGCGTCGAATCACTACGCGCCATTCC | |
| ppc3-R | TCCGTAGCTGAATAGATTCT GCAATCCACG GCAG | |
| ppc4-F | CTGCCGTGGATTGCAGAATCTATTCAG CTA CGGA | |
| ppc4-R | CCCAAGCTTGAGTCGAAAACGAGGGTGTTA GAACAG(HindIII/Mly1) | |
| asd1-F | CTTTCTGCGTGCTAACAAAGCA | For mutating the HindIII site of asd gene |
| Asd1-R | CATCCGCTTTCACGGAGCTT TGGATAGATT TCG | |
| Asd2-F | CGAAATCTATCCAAAGCTCCGTGA AAGCG GATG | |
| Asd2-R | CCCAAGCTTGAGTCGCTCTATTTAACTCCC GGTAAATC(HindIII/MlyI) | |
| pntA/B1-F | CCACTATCACGGCTGAATC | For mutating the MlyI site of pntAB gene |
| pntA/B 1-R | CGGCACAGAATCCATCGCCA TCACGGT | |
| pntA/B2-F | ACCGTGATGGCGATGGATTC TGTGCCG | |
| pntA/B2-R | GCCTTCATGGAATCAACCAT TTCACGGGT | |
| pntA/B3-F | ACCCGTGAAATGGTTGAATCCATGAAGGC | |
| pntA/B3-R | CAGCATGCGCTGAGTAACGG TGAAGCCA CC GA | |
| pntA/B4-F | TCGGTGGCTTCACCGTTACT CAGCGCATGC TG | |
| pntA/B4-R | ACCAGCAATCGGACTTTTCG GATCATCCTG C | |
| pntA/B5-F | GCAGGATGATCCGAAAAGTCCGATTGC TGGT | |

-continued

| Name of primer | Sequence (5'-3') | Remarks |
|---|---|---|
| pntA/B5-R | CCCAAGCTTGAGTCTGGGTATGCT GCTTT CCGT (HindIII/MlyI) | |
| rhtA-F | CCCAAGCTTGAGTCAAAGGATGCCTGGTT CATTACGT(Hind/IIIMlyI) | For amplifying rhtA gene |
| rhtA-R | CTAATAGTGGTAACAAGCGTGA | |
| rhtB-F | CCCAAGCTTGAGTCTCATCATGACCTTAGA ATGGTGGT(HindIII/MlyI) | For amplifying rhtB gene |
| rhtB-R | GCGTGGTTTACCGTCGTT | |
| rhtC-F | CCCAAGCTTGAGTCAATGTATGTTGATGTT ATTTCTCACCGT(HindIII/MlyI) | For amplifying rhtC gene |
| rhtC-R | CTTGCTCAAC GGATTGCTCT | |
| yecC-F | CCCAAGCTTGAGTCCCAAAATGAGTGCCAT TGAAGT(HindIII/MlyI) | For amplifying yecC gene |
| yecC-R | AGTTATGCTGATTTGTTAAGCAGT | |
| T-F | CCCAAGCTTGAGTCCCAAACAATTCCGACG TCTAAGAAG (HindIII/MlyI) | For Overlap PCR to splice the pT-BCD1 fragment |
| TBCD-R | CTCCTTTTTAAGTGAACTTGGGCCCGGTCAG TGCGTCCTG CTGA | |
| TBCD-F | TCAGCAGGACGCACTGACCGGGCCCAAGTT CACTTAAAAGGAG | |
| BCD-R | TAGAAAGTCT CCTGTGCATG A | |
| For CRISPR array | | |
| TGB-F | AGGGAGAAAGGCGGACAGGTTTCCGGTAA GCGGCAGGGTC | For mutating the BciVI site in the |
| TGB-R | GACCCTGCCGCTTACCGGAAACCTGTCCGC CTTTCTCCCT | pTaregetF plasmid |
| N20-ilvA-F | TCCTAGGTATAATACTAGTCTTCATCAAAGTTC GCGCCGGTTTTAGAGCT AGAAATAGC | For constructing the pTargetF-ilvA |
| N20-ilvA-R | GCTATTTCTAGCTCTAAAACCGGCGCGAACTTT GATGAAGACTAGTATTA TACCTAGGA | plasmid |
| N20-tdh-R | TCCTAGGTATAATACTAGTCTTTGGCGACGTTAA CCGCAGTTTTAGAGCTAGAAATAGC | For constructing the pTargetF-tdh |
| N20-tdh-R | GCTATTTCTAGCTCTAAAACTGCGGTTAACGTC GCCAAAGACTAGTATTA TACCTAGGA | plasmid |
| ilv1-F | CTACGAAGGTGCATTGAAGGGGATGCAGGAA ATGCTCTAC | For amplifying the ilvA upstream gene |
| ilv1-R | GCGCTATCAGGCATTTTTCCTATTAACCCCCC AGTTTCGAT | editing template |
| ilv2-F | ATCGAAACTGGGGGGTTAATAGGAAA AATGC CTGAT AGCGC | For amplifying the ilvA downstream |
| ilv2-R | AGTTGGAGAACAGGTACGGACGTAATCAGGT GTCGGTAGA | gene editing template |
| tdh$^1$-F | TCTACCGACACCTGATTACGTCCGTACCTG TTCTCCAACT | For amplifying the tdh upstream gene |
| tdh$^1$-R | GAATACCAGCCCCTTGTTCGTCTCACATCCTCA GGCGATAA | editing template |
| tdh$^2$-F | TTATCGCCTGAGGATGTGAGACG AACAAGGGCT GGTATTC | For amplifying the tdh downstream |
| tdh$^2$-R | CGCGGATCCCAGAATTATCCGTTGAACCAT CGT(BamHI) | gene editing template |
| sgRNA-F | CCCAAGCTTGTATCCCGCTTACCTTGACAGCT AGCTCAGT(HindIII/BciVI) | For amplifying the pJ23119 promoter and |
| sgRNA-R | TGCAGGTCGA CTCTAGAGA | CRISPR gRNA sequences |
| TG-F | GAACTCGAGT AGGGATAACAG | |
| ilvA-I-F | ACGATGCG GTAGAAGCGA TTCT | For ilvA gene |
| ilvA-I-R | GAGAATCTGGCAGTAGTGCTGAT | knockout identification |
| tdh-I-F | ATATTATCAC CGGTACGCTT GGT | For tdh gene |
| tdh-I-R | GCCTGATGCAACAAACGAACGT | knockout identification |

Figure 6:
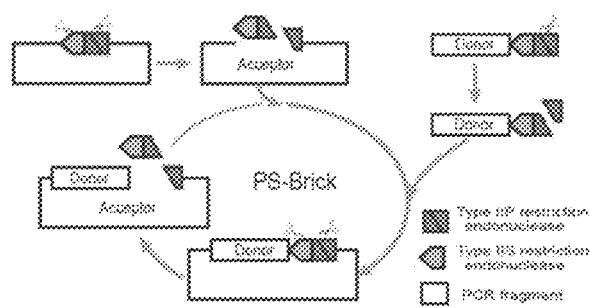
FIG. 6 shows the design principle of PS-Brick assembly in repeat sequence splicing.

As shown in FIG. 1 and FIG. 6, the PS-Brick method is mainly based on whether DNA polymerase has the property of adding A base at the 3' end and the sticky end cleavage feature of Type IIS RE during DNA fragment amplification. During the PCR amplification of the DNA fragment, the Type IIP/IIS double RE site is added at the 5' end by using the primers, the 3' end is not modified, and the type of DNA polymerase is determined by the Type IIS RE used. For the initial vector, a DNA modification method is carried out so that it only contains the same Type IIP/IIS double RE site as the fragment. During DNA fragment assembly, the DNA fragment is subjected to single digestion with Type IIP RE, and the vector is digested with Type IIP and Type IIS REs. The vector after ligation of the DNA fragment still maintains a single type IIP/type IIS double-cleavage site. The double-cleavage site allows for the cyclic assembly of the second round, the third round . . . .

In order to verify the feasibility of this method, Type IIP RE SphI and two Type IIS REs BmrI (producing sticky ends of 1 nt base after cleavage) and MlyI (producing blunt ends after cleavage) are selected to study the application effect of different Type IIS REs. As shown in FIG. 1A, for the SphI/BmrI combination, the DNA fragment is amplified using Taq DNA Polymerase to have a prominent A base at the 3' end, and a SphI/BmrI double-cleavage site is added to the 5' end using a forward primer. As shown in FIG. 1B, for the SphI/MlyI combination, the DNA fragment is amplified with KAPA DNA Polymerase so that the 3' end is blunt-ended, and the SphI/MlyI double-cleavage site is also added to the 5' end by a primer. The corresponding original vectors pOB and pOM of the two combinations are modified by a certain method to have a single SphI/BmrI or SphI/MlyI double-cleavage site.

Example 1

(I) Construction of Original Vectors pOB Plasmid and pOM Plasmid for PS-Brick

Plasmid pUC19 (SEQ ID NO. 1) is used as a basic vector for verifying the PS-Brick assembly method. One BmrI site and three MlyI sites in the vector are removed through overlap extension PCR method (Ho, S N, Hunt, H D, Horton, R M, Pullen, J. K, and Pease, L. R (1989) Site-Directed Mutagenesis by Overlap Extension Using the Polymerase Chain-Reaction, Gene 77, 51-59). Specifically, two DNA fragments are first obtained through amplification using primer pairs UC709-F/UC1179-R and UC1179-F/UC1695-R, respectively, and the two DNA fragments are further spliced by overlap PCR using a primer pair UC709-F/UC1746-R. By using the splicing product as a large primer and the plasmid pUC19 as a template, one of the BmrI sites and three MlyI sites are mutated. Other two BmrI sites and MlyI sites in the multiple cloning site sequence on the plasmid pUC19 are removed by double-cleavage with SphI and NdeI to obtain a pUC19 vector backbone without BmrI and MlyI sites.

With the pSEV A237R vector (Martinez-Garcia, E., Aparicio, T., Goni-Moreno, A., Fraile, S., and de Lorenzo, V. (2015) SEVA 2.0: an update of the Standard European Vector Architecture for de-/re-construction of bacterial functionalities, Nucleic Acids Res 43, D1183-D1189) as a template, PCR amplification is carried out respectively using the same forward primer mC-F and different reverse primers mCB-R (carrying adjacent SphI/BmrI sites) and mCM-R (carrying adjacent SphI/MlyI sites) to obtain two different mCherry truncated fragments. The truncated site is located in the MlyI reverse recognition site "GACTC" (FIG. 2A), which is the only one present in the mCherry gene (SEQ ID NO. 2). Therefore, only the SphI, BmrI and MlyI sites carried by mCB-R and mCM-R are present in the PCR fragments to be integrated (i.e., the mCherry truncated fragments).

The Kapa hot-start high-fidelity polymerase is used to carry out PCR reaction on the above two PCR fragments to be integrated. The reaction cycle is carried out at 95° C. for 3 min for one cycle, 98° C. for 20 s, 65° C. for 20 s, 72° C. for 30 s, totaling 27 cycles and finally at 72° C. for 1 min. The PCR products are purified and recovered, and the DNA concentration is determined using Nanodrop 2000c (Thermo Fisher Company).

The purified PCR products are double digested with SphI and NdeI and ligated to the above pUC19 vector backbone without BmrI and MlyI sites, respectively. By sequencing, the pOB plasmid with the SphI/MlyI adjacent sites and the pOM plasmid with the SphI/BmrI adjacent sites are obtained as PS-Brick original vectors (FIG. 1).

(II) DNA Fragment Assembly

The PCR product FB amplified by Ex-Taq polymerase and the primer FB-R carrying the SphI/BmrI site and the primer FB-F is used as an insert for the TA clone (FIG. 1A), and the PCR product FM amplified by KAPA hot-start high-fidelity polymerase and the primer FM-R carrying the SphI/MlyI sites and the primer FM-F is used as an insert ligated to the blunt end (FIG. 1B). With the pSEV A237R vector (Martinez-Garcia, E., Aparicio, T., Goni-Moreno, A., Fraile, S., and de Lorenzo, V. (2015) SEVA 2.0: an update of the Standard European Vector Architecture for de-/re-construction of bacterial functionalities, Nucleic Acids Res 43, D1183-D1189) as a template, the PCR reaction using Kapa hot-start high-fidelity polymerase is carried out under the same condition as above.

The PCR reaction using Ex-Taq polymerase were as follows: pre-denaturation at 94° C. for 5 min, further at 94° C. for 30 s, at 54° C. for 30 s and at 72° C. for 30 s, totaling 27 cycles and extension at 72° C. for 5 min. After completion of PCR using Ex-Taq polymerase or Kapa hot-start high-fidelity polymerase, the PCR product is gel electrophoresed, and stripes of correct size are cut out, purified by column, and then digested with SphI.

Figure 2:
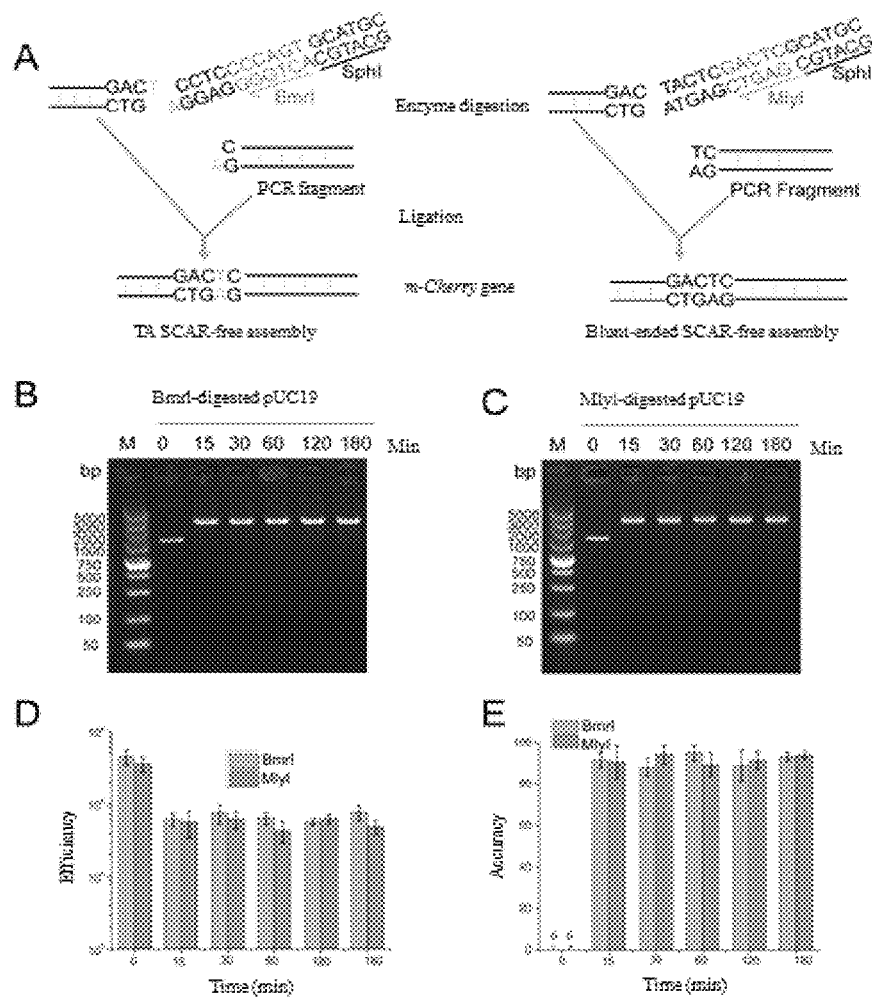
FIG. 2 is an optimization of the reaction conditions of the PS-Brick assembly of Example 2, wherein ordinate unit of the D is CFUs/µg plasmid DNA, and ordinate unit of the E is %.

PS-Brick original vectors pOB and pOM are digested with BmrI and MlyI for 15 min, respectively. The linearized vectors are separated by gel electrophoresis. After column purification, the vectors are digested with SphI for the second time for 15 min, and then heat inactivated at 60° C. for 20 min and then column purified. After two digestions, the recognition site of Type IIS BmrI or MlyI and half of the Type IIP SphI site are detached from the original vector backbone, and BmrI produces a sticky end with 1-nt at one end of the vector (or MlyI produces a blunt end), and SphI produces a sticky end with 4-nt at the other end of the vector (FIG. 1). The purified pOB is ligated to the purified FB, and the purified pOM is ligated to the purified FM. The PCR products (i.e., purified FB or FM) with the single-end suspension of the same adjacent restriction sites (SphI/BmrI or SphI/MlyI) using SphI single digestion have a 4-nt sticky end complementary to the vectors. The 1-nt sticky end of the vector pOB is ligated to the A-added end produced by Ex-Taq polymerase amplified FB (FIG. 1A). The blunt ends of the vector pOM are ligated to the blunt ends of the Kapa hot-start high-fidelity polymerase amplified FM (FIG. 1B). The TA junction or the blunt end junction does not introduce any SCAR sequences, thus achieving SCAR-free assembly (FIG. 2A). The newly assembled vector also contains only one SphI/BmrI or SphI/MlyI adjacent endonuclease sequence pair as the entrance site for the next round of assembly, achieving cyclic recursive assembly (FIG. 1). Therefore, PS-Brick technique can simultaneously achieve recursive and SCAR-free assembly of DNA fragments.

Enzyme digestion systems of all of the above REs are 50 μl, containing 20 units of enzyme and 1 μg of DNA, reacting at 37° C. The 10 μl of ligation reaction system containing 1 μL of T4 DNA ligase, 20 ng of linearized vector and 5-fold molar weight of inserted DNA fragment is incubated at 25° C. for 15 minutes, then placed on ice and transformed into 100 μL of homemade $E.\ coli$ DH5a competent cells (the efficiency of transforming the pUC19 plasmid is $(1.17\pm0.19)\times10^6$ CFU/μg DNA). Primers UC1-6 are used for PCR identification of transformant colonies.

Example 2 Optimization of Reaction Conditions for PS-Brick Assembly

The pOB and pOM vectors are single digested with Type IIS REs BmrI and MlyI, respectively. The digestion reaction system is as described in Example 1, and the reaction time lasts from 15 minutes to 180 minutes according to the reaction conditions of Time-Saver product, followed by electrophoresis to detect cleavage efficiency. As shown in FIG. 2B and FIG. 2C, almost all of the vectors are completely cut in 15 minutes, resulting in a single stripe of linearized size.

The BmrI-cleaved pOB and MlyI-cleaved pOM stripes are recovered with gel, further digested with SphI for 15-180 minutes, inactivated at 65° C., and recovered and ligated to SphSphI-digested PCR products FB and FM, respectively, and transformed into *Escherichia coli*. DH5α competent cells. The transform on units (CFUs) represent DNA assembly efficiency. Twenty clones are picked and sequenced, and the proportion of correctly assembled clones is used as the accuracy of the assembly method.

The SphI single-digested DNA fragments are ligated to the corresponding double-digested vectors under different enzyme digestion time conditions of SphI. The conversion and correct rate of PS-Brick ligation are determined by colony count and PCR identification of transformants. The results show that the conversion rates in the case of the SphI/BmrI combination and in the case of the SphI/MlyI combination both reach $10^4$-$10^5$ cfu/μg DNA under different enzyme digestion time (FIG. 2D), and the correct rates both reach 90% or above (FIG. 2E).

Figure 5:
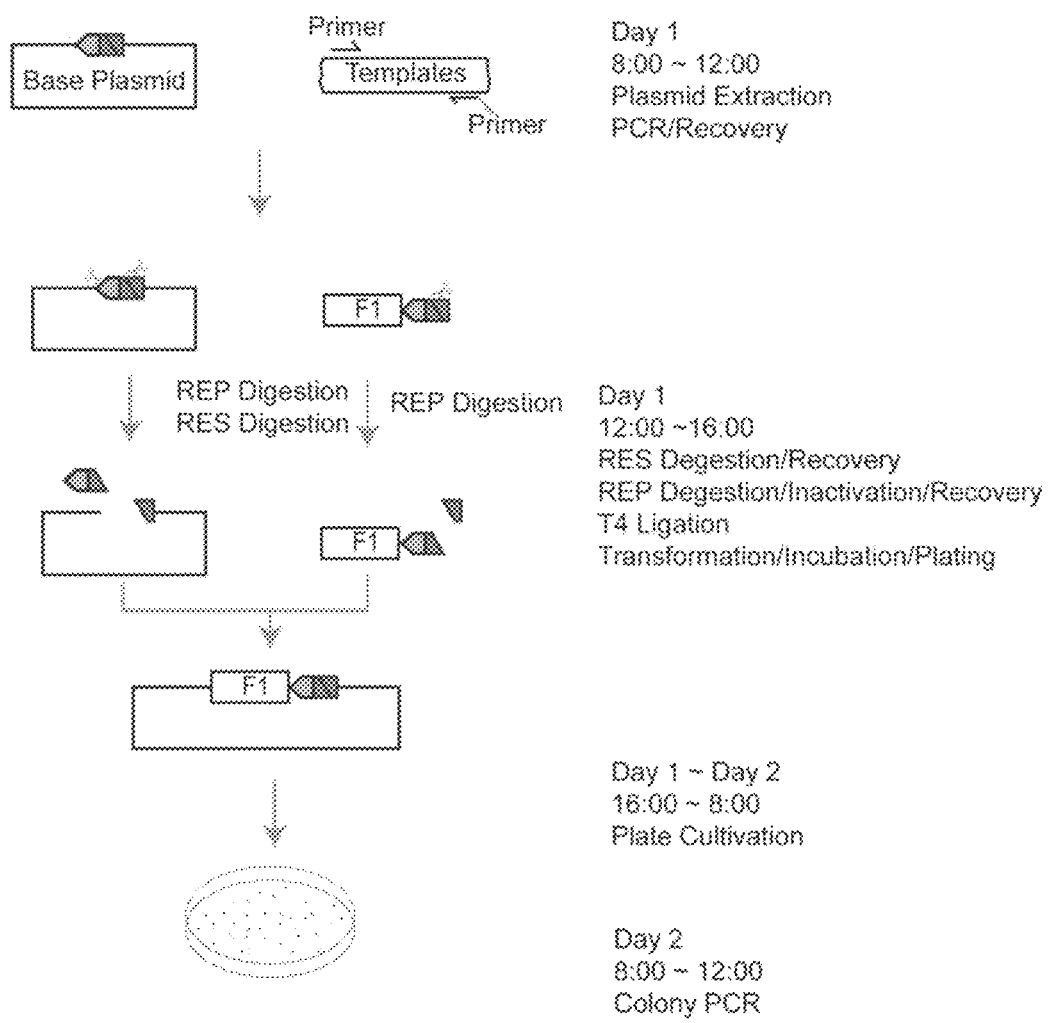
FIG. 5 is a specific time process of PS-Brick assembly in repeat sequence splicing, wherein the REP enzyme is a Type IIP RE, and the RES enzyme is a Rype IIS RE.

The above results indicate that the 15-minute digestion time is sufficient for the Type IIS and IIP REs used in the present example. Taking into account 30 minutes for each of two DNA recovery operations, 20 minutes for RE inactivation, 30 minutes for DNA ligation, 30 minutes for reversal and 40 minutes for resuscitation, PS-Brick's main experimental procedure can be completed in half a day (FIG. 5); further considering the time for PCR amplification, cloning, and identification, each round of PS-Brick can be completed in two days.

Example 3 Engineering of Threonine Metabolic Pathway Using PS-Brick Method

The PS-Brick assembly technique is used to carry out the "design-build-test" cycle of multiple iterations, thus constructing the engineered strain producing threonine. Since gene expression in organisms and the regulation and interaction of signaling networks are very complex, and there is a lack of prior knowledge for predicting how a DNA assembly introduced into a cell can function, multiple versions of the construct need to be tested to obtain an optimal assembly plan. Multiple rounds of step-by-step "design-build-test" experiments require iterative DNA assembly methods.

Figure 3:
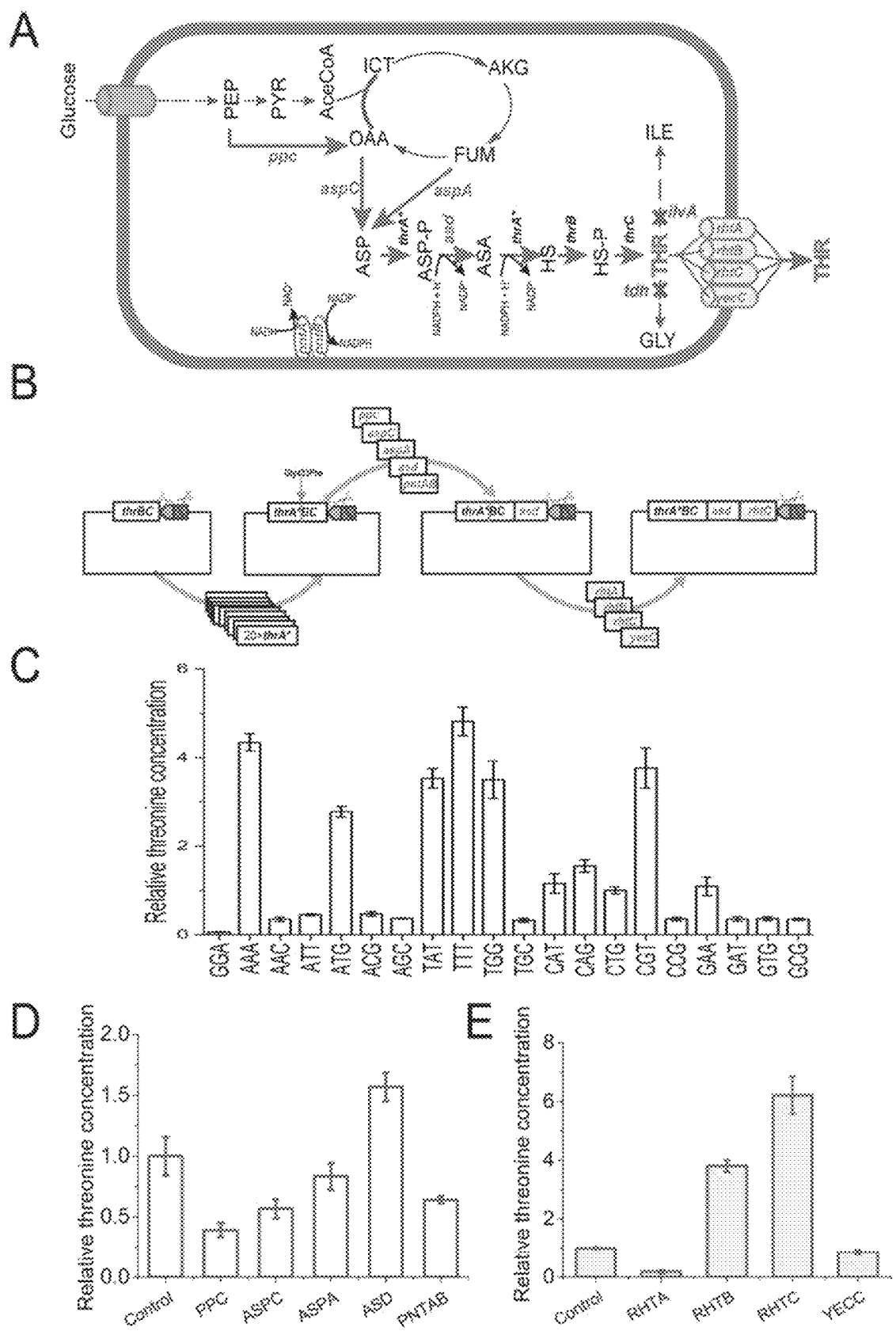
FIG. 3 is a diagram showing the application of the PS-Brick assembly in the metabolic engineering breeding of threonine of Example 3, wherein the threonine yield in C, D and E is relative threonine yield.

The metabolic engineering strategy for constructing a threonine-engineered strain usually includes the following steps: releasing the feedback inhibition of the threonine operon, enhancing the threonine terminal synthesis pathway, removing the metabolic bottleneck, blocking the threonine catabolism, modifying the threonine transport system and enhancing cofactor regeneration (FIG. 3A). Each step of the metabolic engineering process is optimized by a round of the "design-build-test" cycle, and each round of the "design-build-test" cycle is implemented by the PS-Brick assembly technique (FIG. 3B). Recursive PS-Brick assembly technique can achieve multiple rounds of "design-build-test" cycle, thereby gradually modifying the metabolic pathways of the engineered strain and increasing the accumulation of threonine in the engineered strain. In addition to applying the recursive characteristics of the PS-Brick assembly technique, this embodiment also utilizes the advantages of the method for SCAR-free assembly to achieve codon saturation mutagenesis and precise splicing of bicistronics. In addition, this example also exploits the advantages of tandem repeat fragment assembly of the PS-Brick assembly technique to assemble a tandem CRISSPR sgRNA repeat sequence with the same promoter and terminator and knock out two threonine decomposition pathways.

(I) SCAR-Free Fusion of ThrA to Achieve Codon Saturation Mutagenesis

This example uses HindIII and MlyI as the Type IIP and IIS REs for PS-Brick assembly, respectively. Three MlyI sites on the plasmid pACYC184 (SEQ ID NO. 3) are mutated with the primer pairs AC3211-F/AC727-R and AC727-F/AC1143-R by overlap extension PCR and the other MlyI site located at the multiple cloning site is removed through double digestion with HindIII and NruI REs.

The truncated thrABC operon (SEQ ID NO. 4) is amplified using three pairs of primers TAB-F/TAB-R, TBC-F/TBC-R and TC-F/TC-R for overlapping PCR. The RE NruI site is designed to be outside the primer of thrC, and the adjacent HindIII and MlyI restriction sites are designed to be outside the truncation site of thrA (FIG. 3B). The pACYC184 vector backbone of the MlyI site is ligated with the truncated thrABC operon PCR product to obtain the original vector pOthr containing a HindIII/MlyI entrance site for next codon saturation mutagenesis fusion of the thrA gene (FIG. 3B).

The thrA insert for the next step is amplified using Kapa hot-start high-fidelity polymerase. The adjacent HindIII and MlyI restriction sites are designed to be outside the forward primer TA-F, and the 20 reverse primers $TA^{AA}$-R respectively carry a codon sequence causing saturation mutagenesis in the 433th residue of ThrA. Twenty PCR products are digested with HindIII and ligated with HindIII and MlyI double-digested pOthr vectors, respectively, to obtain 20 $pthrA^{433}BC$ SCAR-free spliced saturated mutant vectors. These vectors contain the same HindIII/MlyI site for the next round of DNA assembly.

The obtained expression vectors containing 20 different thrA* mutant sequences are transferred into *E. coli* MG 1655. The shake flask fermentation and comparison are carried out for 12 hours, the threonine yields of the engineered strains overexpressing different mutants are quite different (FIG. 3C), and the type of point mutation that best deactivates feedback inhibition is selected. The experimental results show that the engineered strain transferred to the $pthrA^{Gly433Phe}BC$ vector has the highest threonine yield of 0.39±0.04 g/L, which is 6.5 times that of the wild type control.

So far, $thrA^{433}BC$ described below refers to $thrA^{Gly433}PheBC$.

(II) Identification of Metabolic Bottlenecks of Threonine Biosynthesis

In order to identify the metabolic bottlenecks of threonine biosynthesis, a total of five key enzyme genes, i.e., aspA (SEQ ID NO. 5), aspC (SEQ ID NO. 5), ppc (SEQ ID NO. 7), asd (SEQ ID NO. 8) and pntAB (SEQ ID NO. 9) are selected and ligated to the $thrA^{Gly433}Phe$ vector, respectively, as described above. The aspA gene is amplified using the primers aspA-F/aspA-R, and the aspC gene is amplified using the primers aspC1-F/aspC1-R and aspC2-F/aspC2-R; the ppc gene is amplified using the primers ppc1-F/ppc1-R, ppc2-F/ppc2-R, ppc3-F/ppc3-R and ppc4-F/R; the asd gene is amplified using the primers asd1-F/asd1-R and asd2-F/asd2-R; the pntAB gene is amplified using the primers pntA/B1-F/pntA/B1-R, pntA/B2-F/pntA/B2-R, pntA/B3-F/pntA/B3-R, pntA/B4-F/pntA/B4-R and pntA/B5-F/pntA/B5-R. The PCR products are respectively ligated to the vector $pthrA^{433phe}BC$ by the second round of PS-Brick reaction and transformed into DH5α competent cells, and the correct vector pACYC184-thrA$^{433}$BC-ppc/aspA/aspC/asd/pntAB, is sequenced and transformed to *E. coli*MG655. After the shake flask fermentation for 12 h, the threonine yields of the strains carrying different vectors are determined. The results show that the engineered strain carrying the pACYC184-thrA$^{433}$BC-asd vector has the highest yield of threonine, which is 56.7% higher than the control strain (*E. coli* MG1655/pACYC184-thrA$^{433}$BC) (FIG. 3D); and compared with the control strain, the engineered strains overexpressing the other four genes are not increased in the accumulation of threonine, indicating that the asd gene is a threonine synthesis restriction step of the threonine operon following the overexpression to release feedback inhibition.

(III) Screening of Threonine Efflux Transporter

Further, four threonine efflux transporter genes rhtA (SEQ ID NO. 12), rhtB (SEQ ID NO. 13), rhtC (SEQ ID NO. 14), yecC (SEQ ID NO. 15) are respectively assembled on the pACYC184-thrA$^{433}$ BC-asd vector. The rhtA gene is amplified using the primer rhtA-F/rhtA-R, the rhtB gene is amplified using the primer rhtB-F/rhtB-R, the rhtC gene is amplified using the primer rhtC-F/rhtC-R, and the yecC gene is amplified using the primer yec-F/yec-R. The PCR products are ligated to the vector pACYC184-thrA$^{433}$ BC-asd by a third round of PS-Brick reaction to obtain four vectors pACYC184-thrA$^{433}$ BC-asd-rhtA/rhtB/rhtC/yecC, respectively. Further, the primers T-F/TBCD-R and TBCD-F/BCD-R are used to splice the amplification promoter PT (SEQ ID NO. 10) and the bicistronic design element BCD1 (SEQ ID NO. 11), and the PCR products are ligated to the vectors pACYC184-thrA$^{433}$ BC-asd-rhtA/rhtB/rhtC/yecC respectively by a fourth round of PS-Brick reaction to obtain pACYC184-thrA$^{433}$ BC-asd-P$_T$BCD1-rhtA/rhtB/rhtC/yecC (FIG. 3B). It should be emphasized that the characteristics of the SCAR-free PS-Brick assembly ensure the precise splicing of the translation initiation element BCD1 and the start codon, that is, the last base A of the stop codon UAA of the BCD1 element coincides with the first base A of the start codon ATG of the downstream fusion gene (UAAUG). Through the third and fourth rounds of PS-Brick assembly, four threonine efflux transporter genes overexpressed under the regulation of the same transcriptional and translational initiation elements are obtained. After shake flask fermentation, with *E. coli* MG655/pACYC184-thrA$^{433}$BC-asd as the control strain, the optimal isozyme is screened. As shown in FIG. 3E, the engineered bacteria overexpressing the rhtC gene has the highest accumulation of threonine.

(IV) Blocking of Catabolic Pathway of Threonine

In the above examples, the key gene for threonine synthesis is gradually integrated on the expression vector based on the RE MlyI blunt-ligated PS-Brick method. In this example, a CRISPR sgRNA repeat sequence for knocking out the threonine catabolic pathway gene is assembled based on the PS-Brick method using TA clone of BciVI restriction endonuclease.

Figure 4:
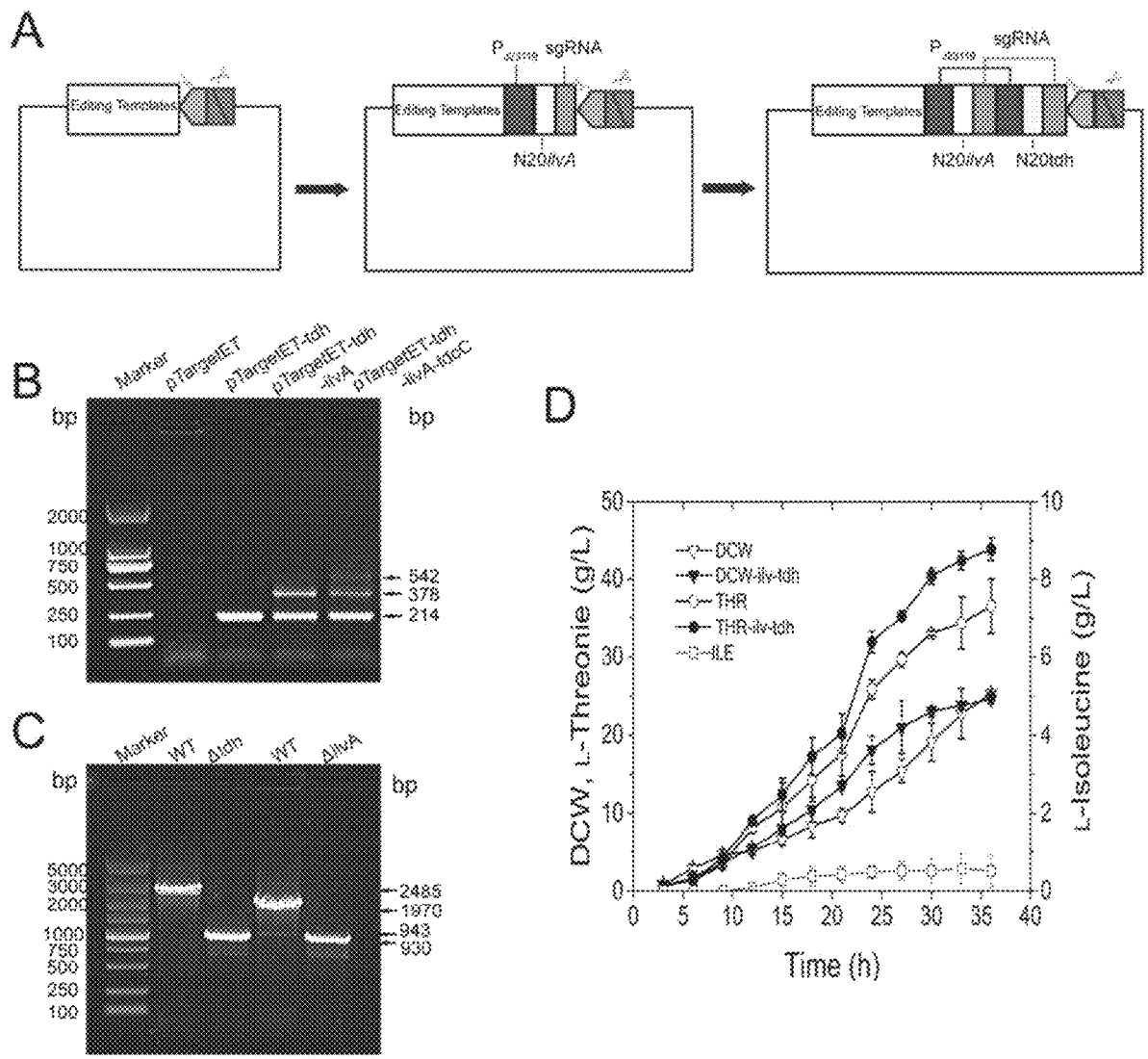
FIG. 4 is a diagram showing the application of the PS-Brick assembly in the metabolic engineering breeding of threonine of Example 3, wherein, in C, WT is wild type, Δtdh is to verify whether to knock out tdh gene, and ΔilvA is to verify whether to knock out ilvA gene; in D, DCW is the dry weight of the control strain, DCW-ilv-tdh is the dry weight of the engineered strain with the i/v and tdh genes knocked out, THR is the threonine yield of the control strain, and THR-ilv-tdh is the threonine yield of the knockout strain, and ILE is isoleucine accumulation of the control strain.

The reported CRISPR-Cas9 gene editing system containing pCas9 and pTargetF vectors (Jiang, Y., Chen, B., Duan, C. L, Sun, B. B, Yang, J. J, and Yang, S. (2015) Multigene Editing in The *Escherichia coli* Genome via the CRISPR-Cas9 System, Appl Environ Microb 81, 2506-2514) is used to knock out the tdh gene (SEQ ID NO. 17) and the ilvA gene (SEQ ID NO. 16). The BciVI site in the pTargetF plasmid is mutated using the primer TGB-F/R for PCR and DpnI digestion and transformation. The donor DNA contains a homologous sequence of 500 base pairs at upstream and downstream of the target genes ilvA and tdh as a template for gene editing. Editing templates for the three target genes are spliced by overlap PCR using primers ilv1/2-F/R and tdh1/2-F/R. The adjacent HindIII-BciVI RE site is designed to be outside the primer ilv1-F, and the BamHI site is designed to be outside the primer tdh2-R. The donor DNA fragment and the pTargetF vector are double digested with REs BamHI and HindIII, and ligated to obtain a ptargetET vector containing a HindIII-BciVI RE site for assembly of the CRISPR sgRNA repeat fragment (FIG. 4A).

First, primers N20-tdh-F/R and N20-ilvA-F/R containing the N20 sequences of tdh and ilvA genes are respectively used for PCR amplification with pTargetF as a template, and the products are recovered and digested with DpnI. The enzyme-digested products are transfected into DH5α competent cells to obtain two vectors pTargetF-tdh and pTargetF-ilv respectively containing the N20 sequences of the tdh and ilvA genes. Next, EX Taq DNA polymerase and the primer sgRNA-F/R are used for PCR amplification with the pTargetF-tdh vector as a template to obtain an sgRNA fragment of the tdh gene (i.e., a fragment containing P$_{J23119}$, tdhN20, and sgRNA) (Jiang, Y., Chen, B., Duan, C. L, Sun, B. B, Yang, J. J, and Yang, S. (2015) Multigene Editing in the *Escherichia coli* Genome via the CRISPR-Cas9 System, Appl Environ Microb 81, 2506-2514). This fragment is single digested with HindIII and ligated to the HindIII/BciVI double-digested ptargetET vector to obtain a ptargetET-tdh vector. This vector contains the HindIII-BciVI site introduced by the primer sgRNA-F as an entrance site for the next round of PS-Brick assembly. EX Taq DNA polymerase and the primer sgRNA-F/R are then used for PCR amplification with the pTargetF-ilv vector as a template to obtain an sgRNA fragment of the ilvA gene. This fragment is single digested with HindIII and ligated to the HindIII/BciVI double-digested ptargetET-tdh vector to obtain the ptargetET-tdh-dv vector (FIG. 4A). Colony PCR is performed using primers TG-F and sgRNA-R, and the correct ptargetET-tdh and ptargetET-tdh-dv vectors are further sequenced.

The vector ptargetET-tdh-ilv containing two identical promoter and terminator sgRNA sequences is constructed by two rounds of PS-Brick assembly, and gene editing is then carried out according to the reference (Jiang, Y., Chen, B., Duan, C. L, Sun, B. B, Yang, J. J, and Yang, S. (2015) Multigene Editing in the *Escherichia coli* Genome via the CRISPR-Cas9 System, Appl Environ Microb 81, 2506-2514). The pTargetET-tdh-ilvA plasmid is transformed into the MG1655/pCas9 competent cells, and then the cells are applied to a double-resistant plate containing 50 mg/L kanamycin and 50 mg/L spectinomycin and cultured at 30° C. Transformants with the ilvA and tdh genes knocked out are identified using primer pairs ilvA-I-F/R and tdh-I-F/R, respectively. The transformants in which the tdh and ilvA genes are successfully knocked out are selected, and the ptargetET-tdh-ilvA and pCas plasmids are sequentially eliminated to obtain *E. coli* G1655ΔtdhΔilvA (FIG. 4C). The plasmid pACYC184-thrA$^{433}$BC-asd-P$_T$BCD1-rhtC constructed above is transformed into *E. coli* MG1655ΔtdhΔilvA to obtain a threonine-producing engineered strain. The fed-batch fermentation is carried out through a 7.5 L fermentor to accumulate 43.9±1.4 g/L threonine, which is 20.3% higher than that of the control strain MG1655/pACYC184-thrA$^{433}$BC-asd-P$_T$BCD1-rhtC in which the tdh and ilvA genes are not knocked out (FIG. 4D), and no by-product isoleucine is detected during the fermentation.

(V) Fermentation Test of Threonine Engineered Strain

In the above description, the shake flask fermentation test method is specifically as follows unless otherwise specified.

Shake flask fermentation test:

1. The test strain is taken, streaked on a solid LB medium plate containing 34 mg/L chloramphenicol, and performed static culture at 37° C. for 12 hours.

2. After step 1, the lawn on the plate is picked up and inoculated into the slant of the LB medium, and performed static culture for 10-12 hours at 37° C.

3. After step 2, the lawn on the plate is picked up, inoculated into liquid LB medium, cultured at 37° C., shaken at 220 rpm for 12 hours to obtain a seed liquid.

4. After step 3, the seed liquid is inoculated into the fermentation medium according to an inoculum volume of 3%, and shaken at 220 rpm and 37° C.

One liter of fermentation medium includes: 80 g/L of MOPS, 20.0 g/L of glucose, 15.0 g/L of ammonium sulfate, 2.0 g/L of monopotassium phosphate, 2.0 g/L of magnesium sulfate heptahydrate, 2.0 g/L of yeast powder, 5 mL/L of a mixed solution of trace elements, and the balance of water.

One liter of the mixed solution of trace elements includes: 10 g/L of $FeSO_4 \cdot 7H_2O$, 1.35 g/L of $CaCl_2$, 2.25 g/L of $ZnSO_4 \cdot 7H_2O$, 0.5 g/L of $MnSO_4 \cdot 4H_2O$, 1 g/L of $CuSO_4 \cdot 5H_2O$, 0.106 g/L $(NH_4)_6Mo_7O_{24} \cdot 4H_2O$, 0.23 g/L of $Na_2B_4O_7 \cdot 10H_2O$, 0.48 g/L of $CoCl_2 \cdot 6H_2O$, 10 mL/L of 35% HCl and the balance of water.

During the culture process, the pH of the reaction system is adjusted with ammonia water to be maintained at 6.8-7.0.

During the culture process, samples are taken every 3-4 hours, and the glucose content is measured using a biosensor analyzer SBA-40D. When the glucose content in the system is less than 5 g/L, glucose is added so that the glucose concentration in the system reaches 10 g/L.

After 24 hours of culture, samples are taken, centrifuged at 12000 g for 2 minutes, and the supernatant is taken to measure the concentration of L-threonine.

In the above description, the fermenter fermentation test method is specifically as follows unless otherwise specified.

Fermenter Fermentation Test:

The method of this example refers to the patent (application No. 201110279419.1), and the seed culture medium used is composed of water and solutes; the concentrations of the solutes in the medium are as follows: glucose 40 g/L, ammonium sulfate 15 g/L, monopotassium phosphate 2 g/L, magnesium sulfate 2 g/L, yeast powder 2 g/L, L-isoleucine 0.05 g/L, calcium carbonate 15 g/L, the mixed solution of trace elements 2 mL/L.

The fermentation initial medium used in this example is composed of water and solutes; the concentrations of the solutes in the medium are as follows: glucose 10 g/L, ammonium sulfate 10 g/L, monopotassium phosphate 2 g/L, magnesium sulfate 2 g/L, yeast powder 2 g/L, and the mixed solution of trace elements 2 mL/L.

The cell yield of *E. coli* MG1655 with L-isoleucine as substrate is determined by pre-experiment to be 107 g/g (i.e., 107 g dry weight of *E. coli* MG1655 cells generated from per gram of L-isoleucine).

1. Obtain seed liquid (1) The test strain stored in a −80° C. cryotube is streaked into the LB medium plate, and incubated in a 37° C. incubator for 12 hours.

(2) The single colony of step (1) is transferred into a test tube containing 3 mL of liquid LB medium, and incubated in 37° C. shaker at 180 rpm for 12 hours.

(3) The bacterial solution of step (2) is transferred in a 500 mL shake flask containing 30 mL of seed culture medium according to an inoculum volume of 3% (volume ratio), and then incubated in a 37° C. shaker at 220 rpm for 12 hours to obtain a seed liquid (OD600=8.5).

2. The seed liquid of step 1 is inoculated into the fermentation initial medium in the fermenter according to an inoculum volume of 3% (volume ratio), and cultured until 3 g (dry weight) of cells is contained per liter of the fermentation liquid, and a total of 2.2 L of fermentation broth is obtained.

In the whole step 2: the fermentation temperature is controlled to be 37° C. by the heating jacket and the cooling water; air is introduced to supply dissolved oxygen, and if necessary, the mixture of oxygen and air is introduced in a ratio of 1:1 (volume ratio), the dissolved oxygen is controlled to be 50% by the rotation speed-dissolved oxygen signal cascade control; the addition of 25% (volume ratio) of ammonia water adjusts the pH and maintains it at 6.8.

3. Feeding is carried out by feed liquid A (L-isoleucine aqueous solution), and a constant speed programmable control pump built in the fermenter is controlled by Bio-Command Plus biological process software to realize index feeding: input the following program: $F=(\mu \cdot X_0 \cdot V_0 \cdot e^{\mu t})/(S \cdot Y_{ile/X})$, where F refers to index feeding rate, $\mu$ refers to the set specific growth rate, and $X_0$ refers to the initial cell concentration (its value is 3 g·L$^{-1}$), $V_0$ is the initial fermentation liquid volume (its value is 2.2 L), e is a natural logarithm (its value is 2.718), t refers to the fermentation time, and S refers to the concentration of L-isoleucine in the feed liquid A (its value is 2 g/L), $Y_{ile/X}$ refers to cell yield (its value is 107 g/g); the specific growth rate is set to be 0.16 h$^{-1}$. The index feeding and fermentation are continued until the growth of the cells does not increase.

In the whole step 3: the fermentation temperature is controlled to be 37° C. by the heating jacket and the cooling water; air is introduced to supply dissolved oxygen, and if necessary, the mixture of oxygen and air is introduced in a ratio of 1:1 (volume ratio), the dissolved oxygen is controlled to be 50% by the rotation speed-dissolved oxygen signal cascade control; the addition of 25% (volume ratio) of ammonia water adjusts the pH and maintains it at 6.8.

During the culture, samples are taken every 3-4 hours, centrifuged at 12000 g for 2 minutes, and the supernatant is taken to measure the concentration of L-threonine.

(VI) Threonine HPLC Detection Method

Method for detecting L-threonine concentration: High-performance liquid phase method, optimized on the basis of the amino acid detection method in the reference (Amino Acids and Biological Resources, 2000, 22, 59-60); the specific method is as follows (2,4-dinitrofluorobenzene (FDBN) pre-column derivatization high-performance liquid phase method):

10 μL of the supernatant is added into a 2 mL centrifuge tube, 200 μL of 0.5 M $NaHCO_3$ aqueous solution and 100 μL of 1% (volume ratio) FDBN-acetonitrile solution are then added, the reaction system is heated in a dark place in a 60° C. water bath for 60 min and then cooled to room temperature; next, 700 μL of 0.04 mol/L $KH_2PO_4$ aqueous solution (pH=7.2±0.05, pH is adjusted with 40 g/L KOH aqueous solution) is added and shaken to be uniform; the reaction system is rested for 15 min and then filtered; the filtrate is collected. The filtrate is used for loading and the sample amount is 15 μL.

The chromatography column is a C18 column (ZORBAX Eclipse XDB-C18, 4.6*150 mm, Agilent, USA); column temperature: 40° C.; UV detection wavelength: 360 nm; mobile phase A is 0.04 mol/L $KH_2PO_4$ aqueous solution (pH=7.2±0.05, the pH is adjusted with 40 g/100 mL of KOH aqueous solution), and mobile phase B is 55% by volume of acetonitrile aqueous solution, and the total flow rate of the mobile phase is 1 mL/min.

Elution process: at the start time of elution (0 min), the volume fraction of mobile phase A in the total flow of mobile phase is 86%, and the volume fraction of mobile phase B in the total flow of the mobile phase is 14%; the elution process is divided into 4 stages. In each stage, the volume fractions of mobile phase A and mobile phase D in the total flow of the mobile phase both change linearly; at the end of the first stage (lasting 2 minutes from the start time), the volume fraction of mobile phase A in the total flow of the mobile phase is 88%, and the volume fraction of mobile phase B in the total flow of the mobile phase is 12%; at the end of the second stage (lasting 2 minutes from the end of the first stage), the volume fraction of the mobile phase A in the total flow of the mobile phase is 86%, and the volume fraction of the mobile phase B in the total flow of the mobile phase is 14%; at the end of the third stage (lasting 6 minutes from the end of the second stage), the volume fraction of the mobile phase A in the total flow of the mobile phase is 70%, and the volume fraction of the mobile phase B in the total flow of the mobile phase is 30%; at the end of the fourth stage (lasting 10 minutes from the end of the third stage), the volume fraction of the mobile phase A in the total flow of the mobile phase is 30%, and the volume fraction of the mobile phase B in the total flow of the mobile phase is 70%.

A standard curve is prepared using commercially available L-threonine as a standard (purchased from sigma, Cat. No. 8917) to calculate the threonine concentrations of the samples.

It should be noted that the above-described examples are merely illustrative of the invention and are not intended to limit the implementations. Other variations or modifications of the various forms may be made by those skilled in the art in light of the above description. There is no need and no way to exhaust all of the implementations. Obvious changes or variations resulting therefrom are still within the scope of the invention.

What is claimed is:

1. A DNA assembly method, comprising:
   (1) performing a single-ended ligation of a gene to be inserted to a DNA fragment containing adjacent Type IIP and Type IIS RE recognition sites to obtain a target gene;
   (2) cleaving the target gene using the corresponding Type IIP RE to obtain a donor DNA with a sticky end;
   (3) cleaving a plasmid using the corresponding Type IIP and Type IIS REs to obtain an acceptor DNA, wherein the plasmid comprises the same Type IIP and Type IIS RE recognition sites as the target gene; and
   (4) ligating the sticky end of donor DNA to the Type IIP RE cleaved complementary sticky end of acceptor DNA and ligating the un-cleaved end of donor DNA to the Type IIS RE cleaved end of acceptor DNA.

2. The method according to claim 1, wherein, in the target gene, the Type IIP RE recognition site is outside the Type IIS RE recognition site.

3. The method according to claim 1, wherein, when the Type ITS RE is a Type IIS RE which cleaves to produce single-base sticky ends, the step (1) further comprises attaching an A base to the other end of the gene to be inserted.

4. The method according to claim 1, wherein, in step (3), the plasmid is first cleaved using a corresponding Type IIP RE to obtain a linearized plasmid, and the linearized plasmid is then cleaved using a corresponding Type IIS RE.

5. A DNA assembly method, comprising:
   (1) performing a single-ended ligation of a gene to be inserted to a DNA fragment containing adjacent Type IIP and Type IIS RE recognition sites to obtain a target gene;
   (2) cleaving the target gene using the corresponding Type IIP RE to obtain a donor DNA with a sticky end;
   (3) cleaving a plasmid using the corresponding Type IIP and Type IIS REs to obtain an acceptor DNA, wherein the plasmid comprises the same Type IIP and Type IIS RE recognition sites as the target gene, wherein the Type IIP RE cleaves to produce sticky ends with two to four bases; and
   (4) ligating the sticky end of donor DNA to the Type IIP RE cleaved complementary sticky end of acceptor DNA and ligating the un-cleaved end of donor DNA to the Type IIS RE cleaved end of acceptor DNA.

6. A DNA assembly method, comprising:
   (1) performing a single-ended ligation of a gene to be inserted to a DNA fragment containing adjacent Type IIP and Type IIS RE recognition sites to obtain a target gene;
   (2) cleaving the target gene using the corresponding Type IIP RE to obtain a donor DNA with a sticky end;
   (3) cleaving a plasmid using the corresponding Type IIP and Type IIS REs to obtain an acceptor DNA, wherein the plasmid comprises the same Type IIP and Type IIS RE recognition sites as the target gene, wherein the Type IIS RE cleaves to produce single-base sticky ends, or cleaves to produce blunt ends; and
   (4) ligating the sticky end of donor DNA to the Type IIP RE cleaved complementary sticky end of acceptor DNA and ligating the un-cleaved end of donor DNA to the Type IIS RE cleaved end of acceptor DNA.

7. A DNA assembly method, comprising:
(1) performing a single-ended ligation of a gene to be inserted to a DNA fragment containing adjacent Type IIP and Type IIS RE recognition sites to obtain a target gene;
(2) cleaving the target gene using the corresponding Type IIP RE to obtain a donor DNA with a sticky end;
(3) cleaving a plasmid using the corresponding Type IIP and Type IIS REs to obtain an acceptor DNA, wherein the plasmid comprises the same Type IIP and Type IIS RE recognition sites as the target gene; wherein the Type IIS RE is BmrI, BciVI, HphI or MlyI; and
(4) ligating the sticky end of donor DNA to the Type IIP RE cleaved complementary sticky end of acceptor DNA and ligating the un-cleaved end of donor DNA to the Type IIS RE cleaved end of acceptor DNA.

* * * * *